United States Patent
DeBrecht et al.

(10) Patent No.: US 8,124,841 B2
(45) Date of Patent: Feb. 28, 2012

(54) TRUNCATION OF THE C-TERMINAL END OF ALPHA-AMYLASE

(75) Inventors: Andrew DeBrecht, Cary, NC (US);
Aron Silverstone, Durham, NC (US);
Yan Zhang, Apex, NC (US);
Shengsheng Zhang, Cary, NC (US);
Xuejun Zhong, Cary, NC (US)

(73) Assignee: Syngenta Participations AG, Basel (CH)

( * ) Notice: Subject to any disclaimer, the term of this patent is extended or adjusted under 35 U.S.C. 154(b) by 280 days.

(21) Appl. No.: 12/603,670

(22) Filed: Oct. 22, 2009

(65) Prior Publication Data

US 2010/0100983 A1    Apr. 22, 2010

Related U.S. Application Data

(60) Provisional application No. 61/107,596, filed on Oct. 22, 2008.

(51) Int. Cl.
*C12N 15/82*    (2006.01)
*C12N 15/56*    (2006.01)
*C12N 5/04*     (2006.01)
*C12N 5/10*     (2006.01)
*A01H 5/00*     (2006.01)
*A01H 5/10*     (2006.01)

(52) U.S. Cl. ............ 800/284; 800/287; 800/320.1; 435/419; 435/204; 435/69.8; 435/412

(58) Field of Classification Search .................. None
See application file for complete search history.

(56) References Cited

FOREIGN PATENT DOCUMENTS
WO    WO 2005/096804    * 10/2005

OTHER PUBLICATIONS

Kramhoft et al., Biochemistry, "Involvement of Individual Subsites and Secondary Substrate Binding Sites in Multiple Attack on Amylose by Barley α-Amylase", (2005) vol. 44, pp. 1824-1832.
Chen, et al., Plant Physiology, "Signal Peptide-Dependent Targeting of a Rice α-Amylase and Cargo Proteins to Plastids and Extracellular Compartments of Plant Cells", (Jul. 2004) vol. 135 pp. 1367-1377.
Chikwamba et al., Proceeding of National Academy of Science, "Localization of a Bacterial Protein in Starch Granules of Transgenic Maize Kernels", (Sep. 2003) vol. 100 pp. 11127-11132.
Chidananda et al., The Journal of Biological Chemistry, Topology of Euglena Chloroplast Protein Precursors Within Endoplasmic Reticulum to Golgi to Chloroplast Transport Vesicles, (Jan. 1999), pp. 457-463.
Keegstra et al., Annual Review Plant Physiol. Plant Mol. Biol., "Chloroplastic Precursors and Their Transport Across the Envelope Membranes", (1989) vol. 40 pp. 471-501.
Chen et al., The Plant Journal, "Expression of α-amylases, Carbohydrate Metabolism, and Autophagy in Cultured Rice Cells is Coordinately Regulated by Sugar Nutrient", (1994) vol. 6(5) pp. 625-636.
Vretland P., FEBS Letters, Immobilization of Ligands for Biospecific Affinity Chromatography Via Their Hydroxyl Groups. The Cyclohexaamylose-β-Amylase System, (1974) vol. 47 pp. 86-89.
Silvanovich et al., Analytical Biochemistry, "Affinity Chromatography of Cereal α-Amylase" (1976) vol. 73, pp. 430-433.
B1 Amy I Full Sequence, Swissport: locus Amy1_HORVU, accession P00693.
Robinson et al., Nature Reviews, Molecular Cell Biology, "Protein Targeting by the twin-arginine Translocation Pathway" (May 2001) vol. 2 pp. 350-355.
Chen, et al., Plant Physiology, "Signal Peptide-Dependent Targeting of a Rice α-Amylase and Cargo Proteins to Plastids and Extracellular Compartments of Plant Cells", (Jul. 2004) vol. 135 pp. 1367-137T.
Vretland R, FEBS Letters, Immobilization of Ligands for Biospecific Affinity Chromatography Via Their Hydroxyl Groups. The Cyclohexaamylose-β-Amylase System, (1974) vol. 47 pp. 86-89.

* cited by examiner

*Primary Examiner* — Paul Roath
(74) *Attorney, Agent, or Firm* — Joshua L. Price

(57) ABSTRACT

The present invention is directed to C-terminal truncated α-amylase polypeptides, nucleic acid sequences encoding the truncated α-amylase polypeptides, and methods of using the same. Further provided are expression cassettes, plants and plant parts expressing the nucleic acid sequence encoding the truncated α-amylase. Expression of the truncated α-amylase in a plant cell results in enhanced accumulation of biologically-active α-amylase, or enhanced secretion of the α-amylase from the plant cell, compared to the accumulation or secretion of a full length α-amylase.

20 Claims, No Drawings

US 8,124,841 B2

TRUNCATION OF THE C-TERMINAL END OF ALPHA-AMYLASE

This application claims benefit of provisional application 61/107,596, filed Oct. 22, 2008.

REFERENCE TO SEQUENCE LISTING SUBMITTED ELECTRONICALLY

The official copy of the sequence listing is submitted electronically via EFS-Web as an ASCII formatted sequence listing with a file named 338917_SequenceListing.txt, created on Apr. 22, 2008, and having a size of 53 kilobytes and is filed concurrently with the specification. The sequence listing contained in this ASCII formatted document is part of the specification and is herein incorporated by reference in its entirety.

FIELD OF THE INVENTION

The present invention generally relates to the field of plant molecular biology, and more specifically, to the creation of plants that express an α-amylase enzyme which provides a desired characteristic to the plant or products thereof.

BACKGROUND OF THE INVENTION

Endo-1,4-α-D-glucan glucohydrolase (α-amylase, EC 3.2.1.1) is currently used in a broad array of industrial applications. These applications include starch hydrolysis for the production of ethanol and high fructose corn syrup, starch soil removal in laundry washing powders and dish-washing detergents, textile de-sizing, the production of modified starches, baking, hydrolysis of oil-field drilling fluids, and paper recycling.

Corn is milled to obtain cornstarch and other corn-milling co-products such as corn gluten feed, corn gluten meal, and corn oil. The starch obtained from the process is often further processed into other products such as derivatized starches and sugars, or fermented to make a variety of products including alcohols or lactic acid. Processing of cornstarch often involves the use of enzymes, in particular, enzymes that hydrolyze and convert starch into fermentable sugars or fructose (e.g., α-amylase).

To produce ethanol, starch containing fractions derived from wet milling or ground grain from dry grinding are further hydrolyzed into fermentable sugars which are then fermented to make ethanol. Several plant starch processing methods exist including a raw starch process, which involves little to no heating of the milled plant material being processed; or higher temperature hydrolysis of starch frequently referred to as "liquefaction". In either of these methods for breaking down starch derived from plants, the conventional process involves the addition of alpha-amylase to the milled plant starch in a slurry tank.

Recently a group of α-amylase genes from nature were identified (Richardson et al. (2002) *J. Biol. Chem.* 277 (29): 26501-26507) and subsequent laboratory evolution of these enzymes identified novel and improved α-amylase enzymes with performance characteristics ideal for the corn dry milling process. Additionally, transgenic plants have been developed in which a α-amylase enzyme is introduced into the plants. These plants perform well in fermentation without the addition of exogenous α-amylase, require much less time for liquefaction, and result in more complete solubilization of starch (U.S. Pat. No. 7,102,057).

SUMMARY OF THE INVENTION

The present invention is directed to C-terminal truncated α-amylase polypeptides, nucleic acid sequences encoding the truncated α-amylase polypeptides, and methods of using the same. Further provided are expression cassettes, plants and plant parts comprising the nucleic acid sequence encoding the truncated α-amylase.

In one embodiment, the present invention is directed to a vector or cell comprising the expression cassettes provided herein. Moreover, the present invention encompasses a plant stably transformed with the vectors of the present invention. A plant stably transformed with a vector comprising a truncated α-amylase having a nucleotide sequence of any of SEQ ID NO: 1, 3, 5, or 7, or a nucleotide sequence encoding the amino acid sequence of SEQ ID NO: 2, 4, 6, or 8 is provided. Expression of the truncated α-amylase in a plant cell results in enhanced accumulation of biologically-active α-amylase, or enhanced secretion of the α-amylase from the plant cell, compared to the accumulation or secretion of a full-length α-amylase.

In one embodiment an expression cassette may be constructed comprising a promoter operably linked to a polynucleotide encoding a truncated α-amylase. Said promoter may be a inducible, tissue-specific or a endosperm-specific promoter. In some aspects a maize gamma zein promoter may be used.

In another embodiment, expression cassettes containing a polynucleotide encoding a truncated α-amylase may comprise one or more signal sequences that may target the truncated α-amylase to various parts of the plant cell. For example, one may want to target the truncated α-amylase to the vacuole, endoplasmic reticulum, chloroplast, seed or cell wall of the plant.

In another embodiment a plant cell, plant or plant seed may be stably transformed with an expression cassette comprising a polynucleotide encoding a truncated α-amylase.

Yet another embodiment, is a method of enhancing a α-amylase to accumulate or secrete at higher levels in plant or plant parts through C-terminal truncation, N-terminal truncation or both C- and N-terminal truncation. Said truncation may be 1 nucleic acid residues, 2 nucleic acid residues, 3 nucleic acid residues, 4 nucleic acid residues, 5 nucleic acid residues, 6 nucleic acid residues, 7 nucleic acid residues, 8 nucleic acid residues, 9 nucleic acid residues or 10 or more nucleic acid residues.

DETAILED DESCRIPTION

The present invention now will be described more fully hereinafter. Many modifications and other embodiments of the inventions set forth herein will come to mind to one skilled in the art to which these inventions pertain having the benefit of the teachings presented in the foregoing descriptions. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation. appended claims. Although specific terms are employed herein, they are used in a generic and descriptive sense only and not for purposes of limitation.

The article "a" and "an" are used herein to refer to one or more than one (i.e., to at least one) of the grammatical object of the article. By way of example, "an element" means one or more element. Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps.

Overview

Transgenic plants expressing a heterologous α-amylase enzyme have been developed for multiple industrial, agricultural, and pharmaceutical applications, including improving food or feed for human or animal consumption, as well as for the production of fermentation feedstock for ethanol production. The term "α-amylase" (e.g., E.C. class 3.2.1.1) refers to enzymes that catalyze the hydrolysis of alpha-1,4-glucosidic linkages. These enzymes have also been described as those effecting the exo or endohydrolysis of 1,4-α-D-glucosidic linkages in polysaccharides containing 1,4-α-linked D-glucose units. Another term used to describe these enzymes is "glycogenase". Expression of α-amylase enzymes in plant material useful in, for example, fermentation processes obviates the need for exogenous addition of purified enzyme, which can be difficult or costly to manufacture.

Thus, plants expressing the α-amylase enzyme are a source of raw material for fermentation processes, as well as a source of the enzymes that facilitate conversion of the raw material into a fermentable product. The plant part comprising the truncated α-amylase enzyme may be treated to physically combine the enzyme with its substrate under conditions which allow the enzyme to be active on the substrate, which will then digest polysaccharides in the plant part to form oligosaccharide or fermentable sugar. The fermentable sugar may be further incubated under conditions that promote the conversion of the fermentable sugar or oligosaccharide into ethanol.

The invention also provides for the production of improved crop varieties that accumulate higher levels of α-amylase in their endosperm or starch accumulating organ. Under conditions such as by boiling, grinding, milling, adding liquid or heating the plant or a part thereof, the enzyme(s) is allowed to come into contact with its substrate and facilitate the rapid conversion of the starch into simple sugars.

In yet another embodiment, recombinantly-produced α-amylase may be prepared by transforming plant tissue or plant cells comprising the truncated α-amylase enzymes of the present invention, selecting for the transformed plant tissue or cell, growing the transformed plant tissue or cell into a transformed plant, and isolating the truncated α-amylase enzyme from the transformed plant or part thereof. The truncated α-amylase enzymes disclosed herein are particularly suitable for such purposes due to the higher accumulation of enzyme in the plant part.

Further provided are methods for accumulating α-amylase in a plant comprising introducing into the plant an expression cassette comprising a nucleotide sequence encoding a truncated α-amylase. While not bound by any particular theory or mechanism, expression of the truncated α-amylase results in accumulation of the enzyme in the plant. In various embodiments, the truncated α-amylase enzyme is expressed in or targeted to a specific tissue or organ, such that the truncated α-amylase accumulates in that tissue or organ. In various embodiments, the accumulation of truncated α-amylase is enhanced relative to the accumulation of full-length α-amylase.

Alpha-Amylase

A variety of α-amylase enzymes have been identified from nature or engineered using modern molecular techniques to generate altered or improved enzymes. However, the level of expression and/or accumulation of active enzymes in transgenic plant material has been insufficient or suboptimal for certain downstream applications.

Provided herein are C-terminal truncated α-amylase enzymes derived from the full length barley α-amylase enzyme. These truncated α-amylase enzymes, when expressed in a plant cell, accumulate to significantly higher levels than the full length α-amylase enzyme. By "C-terminal truncated α-amylase enzyme," or "truncated α-amylase," is intended an amino acid sequence corresponding to amino acid positions 1 through 405 of SEQ ID NO:10, a nucleotide sequence corresponding to nucleotide positions 1-1215 of SEQ ID NO:9, or a nucleotide sequence encoding an amino acid sequence corresponding to amino acid positions 1 through 405 of SEQ ID NO:10. The term "native" or "wild type" refers to an α-amylase that is present in the genome of an untransformed cell, i.e., a cell not having a known mutation. For the purposes of the present invention, the "full length" α-amylase enzyme is the barley α-amylase enzyme set forth in SEQ ID NO:9 and 10.

In one embodiment, the nucleotide sequence encoding the truncated α-amylase of the present invention is set forth in SEQ ID NO:1 or 3. In another embodiment, the nucleotide sequence encoding the truncated α-amylase is a nucleotide sequence that encodes the amino acid sequence set forth in SEQ ID NO:2 or 4. The truncated α-amylase can be expressed in a plant or plant part and cultivated under conditions sufficient for the expression and accumulation of the truncated α-amylase protein in the plant or plant part. As used herein, the term "plant part" or "plant tissue" includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like.

In another embodiment, the truncated α-amylase is a biologically-active variant or fragment of the α-amylase-encoding nucleotide sequence disclosed herein as SEQ ID NO:1 or 3, or the α-amylase protein disclosed herein as SEQ ID NO:2 or 4. For nucleotide sequences, variants include those sequences that, because of the degeneracy of the genetic code, encode the identical amino acid sequence of the native protein. Variant nucleotide sequences also include synthetically derived nucleotide sequences (such as those generated, for example, using site-directed mutagenesis) that encode the native protein, as well as those that encode a polypeptide having amino acid substitutions relative to the native protein.

A "variant" amino acid sequence includes polypeptides derived from the reference α-amylase protein by deletion (so-called truncation) or addition of one or more amino acids to the N-terminal and/or C-terminal end of the reference protein; deletion or addition of one or more amino acids at one or more sites in the reference protein (wherein the reference protein is SEQ ID NO:2 or 4); or substitution of one or more amino acids at one or more sites in the reference protein. Such variants may result from, for example, genetic polymorphism or from human manipulation. Methods for such manipulations are generally known in the art.

Moreover, polynucleotides encoding an "enzymatically active" fragment of the truncated α-amylase enzymes described herein are further envisioned. As used herein, "enzymatically active" means a polypeptide fragment of the truncated α-amylase enzyme that has substantially the same biological activity as the truncated or full length α-amylase enzyme to modify the substrate upon which α-amylase normally acts under appropriate conditions.

For the purposes of the present invention, a biologically-active variant or fragment of a truncated α-amylase has substantially the same biological activity as the full length α-amylase and is further characterized by the ability of the truncated α-amylase to accumulate to significantly higher levels in a plant cell, or to be secreted at significantly higher levels from the plant cell, than the full length α-amylase. A "significant increase" is an increase that is larger than the margin of error inherent in the measurement technique, preferably an increase by about 2-fold or greater, by about 3-fold or greater, by about-4-fold or greater. However, it is also contemplated that the increase in accumulation or secretion is any measurable increase including, for example, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or greater increase in accumulation or secretion of the truncated α-amylase.

The level of enzymatic activity can be assessed in a crude or semi-crude extract of the grain or biomass, or the enzyme may be isolated or purified from the grain or biomass and tested for activity. In one embodiment, the grain or biomass is ground to flour and the enzyme is extracted into an appropriate extraction buffer to generate a crude extract. The extract can be centrifuged and the supernatant collected (semi-crude extract). The supernatant is then tested in an assay appropriate for its function. For example, the activity of the truncated α-amylase can be tested by measuring its ability to convert starch into oligosaccharides by methods well known in the art.

To assess whether there is an increase in accumulation or secretion of α-amylase in a plant cell or plant part expressing a truncated α-amylase, the level of protein or transcript can be measured by methods known in the art. While not being bound by any particular theory or mechanism, the truncated enzymes disclosed herein may accumulate to higher levels than the full length amylase due to an increase in the expression and/or stability of the transcript. Where protein accumulation is accompanied by an increase in mRNA expression and/or stability, the level of transcript can be assessed using quantitative polymerase chain reaction assays with primers specific for the truncated genes described herein. Alternatively, or in addition, the level of protein can be assessed using, for example, an immunological detection assay along with an antibody that recognizes α-amylase. Alternatively, the level of enzyme activity can be measured in a sample comprising a plant cell or plant part expressing the truncated α-amylase. In this embodiment, the truncated α-amylase enzymes described herein result in an increase in the amount of enzyme activity detected in a quantity of material derived from the plant or plant part expressing the amylase (e.g., the level of enzyme activity detected in an amount of plant material expressing the amylase, e.g., units of enzyme per gram of plant material). It is understood that the latter description is merely exemplary, and appropriate units of measure will be applied to whatever plant material is being tested.

A biologically-active variant or fragment of the truncated α-amylase nucleotide sequence disclosed herein will encode an amino acid sequence that is truncated at its C-terminus by at least one amino acid residue when compared to the full length α-amylase enzyme set forth in SEQ ID NO:10. In various embodiments, the variant or fragment will be truncated at its C-terminus by at least 2 amino acids, at least about 3 amino acids, at least about 4, at least about 5, at least about 6, at least about 7, at least about 8, at least about 9, at least about 10, at least about 11, at least about 12, at least about 13, at least about 14, at least about 15, at least about 16, at least about 17, at least about 18, at least about 19, at least about 20, or more amino acids, so long as the truncated protein retains biological activity as discussed supra.

The biologically-active variants or fragments may further comprise one or more additions, deletions, or substitutions at the N-terminus or any other region of the α-amylase enzyme, so long as the C-terminus of the encoded enzyme is truncated in comparison to the full length sequence. For example, the biologically-active fragment may comprise at least about 2, at least about 3, at least about 4, at least about 5, at least about 6, at least about 7, at least about 8, at least about 9, at least about 10, at least about 11, at least about 12, at least about 13, at least about 14, at least about 15, at least about 16, at least about 17, at least about 18, at least about 19, at least about 20, or more additions, substitutions, or deletions. In various embodiments, the biologically-active variant or fragment will have at least about 60% sequence identity, at least 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% or greater sequence identity to the amino acid sequence set forth in SEQ ID NO:2 or 4, or to the nucleotide sequence set forth in SEQ ID NO:1 or 3.

The percentage of sequence identity can be determined from alignments performed using algorithms known in the art. The percentage is determined by comparing two optimally aligned sequences over a comparison window, wherein the portion of the sequence in the comparison window may include additions or deletions, including for example gaps or overhangs, as compared to the reference sequence (which does not include additions or deletions) for optimal alignment of the two sequences. The percentage is calculated by determining the number of positions at which the identical nucleotide base or amino acid residue occurs in both sequences to yield the number of matched positions, dividing the number of matched positions by the total number of positions in the window of comparison and multiplying the result by 100 to yield the percentage of sequence identity. As used herein, "reference sequence" is a defined sequence used as a basis for sequence comparison. For the purposes of the present invention, the reference sequence is SEQ ID NO:2 or 4, and, unless otherwise specified, the comparison window is across the entirety of the reference sequence. Under this circumstance, missing amino acids (or nucleotides) at the C-terminus or the N-terminus (or 3' end or 5' end) of the query sequence when compared to the reference sequence are counted as mismatched positions.

Alignment of nucleotide or polypeptide sequences for comparison may be conducted by the local homology algorithm of Smith and Waterman (Add APL Math 2:482 (1981)), by the homology alignment algorithm of Needleman and Wunsch (J. Mol. Biol 48:443 (1970)), by the search for similarity method of Pearson and Lipman (Proc Natl Acad Sci USA 85:2444 (1988)), by computerized implementations of these algorithms, or by inspection. Computer implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. 1988; Higgins et al. 1989; Corpet et al. 1988; Huang et al. 1992; and Pearson et al. 1994. The ALIGN program is based on the algorithm of Myers and Miller, supra. The BLAST programs of Altschul et al., 1990, are based on the algorithm of Karlin and Altschul supra.

When two sequences have been identified for comparison, GAP and BESTFIT are preferably employed to determine their optimal alignment. Typically, the default values of 5.00 for gap weight and 0.30 for gap weight length are used. In a preferred embodiment, percenty identity is determined using the GAP program for global alignment using default parameters, using the version of GAP found in the GCG package (Wisconsin Package Version 10.1, Genetics Computer Group, 575 Science Dr., Madison, Wis.).

To obtain gapped alignments for comparison purposes, Gapped BLAST (in BLAST 2.0) can be utilized as described in Altschul et al. 1997. Alternatively, PSI-BLAST (in BLAST 2.0) can be used to perform an iterated search that detects distant relationships between molecules. See Altschul et al., supra. When utilizing BLAST, Gapped BLAST, PSI-BLAST, the default parameters of the respective programs (e.g. BLASTN for nucleotide sequences, BLASTX for proteins) can be used. The BLASTN program (for nucleotide sequences) uses as defaults a wordlength (W) of 11, an expectation (E) of 10, a cutoff of 100, M=5, Nc=−4, and a comparison of both strands. For amino acid sequences, the BLASTP program uses as defaults a wordlength (W) of 3, an expectation (E) of 10, and the BLOSUM62 scoring matrix (see Henikoff & Henikoff, 1989). See http://www.ncbi.nlm.nih.gov. Alignment may also be performed manually by inspection.

The nucleic acid molecules of the invention can be "optimized" for enhanced expression in plants of interest. See, for example, EPA 035472; WO 91/16432; Perlak et al., 1991; and Murray et al., 1989. In this manner, the open reading frames in genes or gene fragments can be synthesized utilizing plant-preferred codons. See, for example, Campbell and Gowri, 1990 for a discussion of host-preferred codon usage. Thus, the nucleotide sequences can be optimized for expression in any plant. It is recognized that all or any part of the gene sequence may be optimized or synthetic. That is, synthetic or partially optimized sequences may also be used. Variant nucleotide sequences and proteins also encompass sequences and protein derived from a mutagenic and recombinogenic procedure such as DNA shuffling. With such a procedure, one or more different coding sequences can be manipulated to create a new polypeptide possessing the desired properties. In this manner, libraries of recombinant polynucleotides are generated from a population of related sequence polynucleotides comprising sequence regions that have substantial sequence identity and can be homologously recombined in vitro or in vivo. Strategies for such DNA shuffling are known in the art. See, for example, Stemmer, 1994; Stemmer, 1994; Crameri et al., 1997; Moore et al., 1997; Zhang et al., 1997; Crameri et al., 1998; and U.S. Pat. Nos. 5,605,793 and 5,837,458.

Thus, the polypeptides may be altered in various ways including amino acid substitutions, deletions, truncations, and insertions. Methods for such manipulations are generally known in the art. For example, amino acid sequence variants of the polypeptides can be prepared by mutations in the DNA. Methods for mutagenesis and nucleotide sequence alterations are well known in the art. See, for example, Kunkel, 1985; Kunkel et al., 1987; U.S. Pat. No. 4,873,192; Walker and Gaastra, 1983 and the references cited therein. Guidance as to appropriate amino acid substitutions that do not affect biological activity of the protein of interest may be found in the model of Dayhoff et al. (1978). Conservative substitutions, such as exchanging one amino acid with another having similar properties, are preferred.

Individual substitutions, deletions or additions that alter, add or delete a single amino acid or a small percentage of amino acids (typically less than 5%, more typically less than 1%) in an encoded sequence are "conservatively modified variations," where the alterations result in the substitution of an amino acid with a chemically similar amino acid. The crystal structure of barley amylase is known, and various studies have been performed to determine which residues are critical for amylase activity. See, for example, Robert et al. (2005) *Journal of Biological Chemistry* 280(38):32968-32978 and Bozonnet et al. (2007) *FEBS Journal* 274:5055-5067, each of which is incorporated by reference herein in its entirety.

Conservative substitution tables providing functionally similar amino acids are well known in the art. The following five groups each contain amino acids that are conservative substitutions for one another: Aliphatic: Glycine (G), Alanine (A), Valine (V), Leucine (L), Isoleucine (I); Aromatic: Phenylalanine (F), Tyrosine (Y), Tryptophan (W); Sulfur-containing: Methionine (M), Cysteine (C); Basic: Arginine I, Lysine (K), Histidine (H); Acidic: Aspartic acid (D), Glutamic acid (E), Asparagine (N), Glutamine (Q). See also, Creighton, 1984. In addition, individual substitutions, deletions or additions which alter, add or delete a single amino acid or a small percentage of amino acids in an encoded sequence are also "conservatively modified variations."

As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

Expression Cassettes

A plant or plant part expressing a truncated amylase can be obtained by introducing into the plant or plant part a heterologous nucleic acid sequence encoding the truncated amylase. The heterologous nucleic acid sequences may be present in DNA constructs or expression cassettes. "Expression cassette" as used herein means a nucleic acid molecule capable of directing expression of a particular nucleotide sequence in an appropriate host cell, comprising a promoter operatively linked to the heterologous nucleotide sequence of interest (i.e., truncated amylase) which is operatively linked to termination signals. It also typically comprises sequences required for proper translation of the nucleotide sequence. The expression cassette comprising the truncated α-amylase may be chimeric, meaning that at least one of its components is heterologous with respect to at least one of its other components. The expression cassette may also be one that is naturally occurring but has been obtained in a recombinant form useful for heterologous expression. Typically, however, the expression cassette is heterologous with respect to the host. The expression of the nucleotide sequence in the expression cassette may be under the control of a constitutive promoter or of an inducible promoter that initiates transcription only when the host cell is exposed to some particular external stimulus. Additionally, the promoter can also be specific to a particular tissue or organ or stage of development.

The expression cassette may optionally comprise a transcriptional and translational termination region (i.e. termination region) functional in plants. In some embodiments, the expression cassette comprises a selectable marker gene to allow for selection for stable transformants. Expression constructs of the invention may also comprise a leader sequence and/or a sequence allowing for inducible expression of the truncated amylase. See, Guo et al. (2003) *Plant J.* 34:383-92 and Chen et al. (2003) *Plant J* 36:731-40 for examples of sequences allowing for inducible expression.

The regulatory sequences of the expression construct are operably linked to the nucleic acid sequence encoding the truncated amylase. By "operably linked" is intended a functional linkage between a promoter and a second sequence wherein the promoter sequence initiates and mediates transcription of the DNA sequence corresponding to the second sequence. Generally, operably linked means that the nucleotide sequences being linked are contiguous.

Any promoter capable of driving expression in the plant of interest may be used in the practice of the invention. The promoter may be native or analogous or foreign or heterologous to the plant host. The terms "heterologous" and "exogenous" when used herein to refer to a nucleic acid sequence (e.g. a DNA or RNA sequence) or a gene, refer to a sequence that originates from a source foreign to the particular host cell or, if from the same source, is modified from its original form. Thus, a heterologous gene in a host cell includes a gene that is endogenous to the particular host cell but has been modified through, for example, the use of DNA shuffling. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides.

The choice of promoters to be included depends upon several factors, including, but not limited to, efficiency, selectability, inducibility, desired expression level, and cell- or tissue-preferential expression. For example, where expression in specific tissues or organs is desired, tissue-specific promoters may be used. In contrast, where gene expression in response to a stimulus is desired, inducible promoters are the regulatory elements of choice. Where continuous expression is desired throughout the cells of a plant, constitutive promoters are utilized. It is a routine matter for one of skill in the art to modulate the expression of a sequence by appropriately selecting and positioning promoters and other regulatory regions relative to that sequence.

A number of plant promoters have been described with various expression characteristics. Examples of some constitutive promoters which have been described include the rice actin 1 (Wang et al., Mol. Cell. Biol., 12:3399 (1992); U.S. Pat. No. 5,641,876), CaMV 35S (Odell et al., Nature, 313:810 (1985)), CaMV 19S (Lawton et al., 1987), nos (Ebert et al., 1987), Adh (Walker et al., 1987), sucrose synthase (Yang & Russell, 1990), and the ubiquitin promoters.

Vectors for use in tissue-specific targeting of genes in transgenic plants will typically include tissue-specific promoters and may also include other tissue-specific control elements such as enhancer sequences. Promoters which direct specific or enhanced expression in certain plant tissues will be known to those of skill in the art in light of the present disclosure. These include, for example, the rbcS promoter, specific for green tissue; the ocs, nos and mas promoters which have higher activity in roots or wounded leaf tissue; a truncated (−90 to +8) 35S promoter which directs enhanced expression in roots, an α-tubulin gene that directs expression in roots and promoters derived from zein storage protein genes which direct expression in endosperm.

Tissue specific expression may be functionally accomplished by introducing a constitutively expressed gene (all tissues) in combination with an antisense gene that is expressed only in those tissues where the gene product is not desired.

Moreover, several tissue-specific regulated genes and/or promoters have been reported in plants. Some reported tissue-specific genes include the genes encoding the seed storage proteins (such as napin, cruciferin, beta-conglycinin, and phaseolin) zein or oil body proteins (such as oleosin), or genes involved in fatty acid biosynthesis (including acyl carrier protein, stearoyl-ACP desaturase, and fatty acid desaturases (fad 2-1)), and other genes expressed during embryo development (such as Bce4, see, for example, EP 255378 and Kridl et al., Seed Science Research, 1:209 (1991)). Examples of tissue-specific promoters, which have been described include the lectin (Vodkin, Prog. Clin. Biol. Res., 138; 87 (1983); Lindstrom et al., Der. Genet., 11:160 (1990)), corn alcohol dehydrogenase 1 (Vogel et al., 1989; Dennis et al., Nucleic Acids Res., 12:3983 (1984)), corn light harvesting complex (Simpson, 1986; Bansal et al., Proc. Natl. Acad. Sci. USA, 89:3654 (1992)), corn heat shock protein (Odell et al., 1985; Rochester et al., 1986), pea small subunit RuBP carboxylase (Poulsen et al., 1986; Cashmore et al., 1983), Ti plasmid mannopine synthase (Langridge et al., 1989), Ti plasmid nopaline synthase (Langridge et al., 1989), petunia chalcone isomerase (vanTunen et al., EMBO J., 7; 1257 (1988)), bean glycine rich protein 1 (Keller et al., Genes Dev., 3:1639 (1989)), truncated CaMV 35S (Odell et al., Nature, 313:810 (1985)), potato patatin (Wenzler et al., Plant Mol. Biol., 13:347 (1989)), root cell (Yamamoto et al., Nucleic Acids Res., 18:7449 (1990)), maize zein (Reina et al., Nucleic Acids Res., 18:6425 (1990); Kriz et al., Mol. Gen. Genet., 207:90 (1987); Wandelt et al., Nucleic Acids Res., 17:2354 (1989); Langridge et al., Cell, 34:1015 (1983); Reina et al., Nucleic Acids Res., 18:7449 (1990)), globulin-1 (Belanger et al., Genetics, 129:863 (1991)), α-tubulin, cab (Sullivan et al., Mol. Gen. Genet., 215:431 (1989)), PEPCase (Hudspeth & Grula, 1989), R gene complex-associated promoters (Chandler et al., Plant Cell, 1:1175 (1989)), and chalcone synthase promoters (Franken et al., EMBO J., 10:2605 (1991)). Particularly useful for seed-specific expression is the pea vicilin promoter (Czako et al., Mol. Gen. Genet., 235:33 (1992). (See also U.S. Pat. No. 5,625,136, herein incorporated by reference.) Other useful promoters for expression in mature leaves are those that are switched on at the onset of senescence, such as the SAG promoter from *Arabidopsis* (Gan et al., Science, 270:1986 (1995).

A class of fruit-specific promoters expressed at or during anthesis through fruit development, at least until the beginning of ripening, is discussed in U.S. Pat. No. 4,943,674, the disclosure of which is hereby incorporated by reference.

cDNA clones that are preferentially expressed in cotton fiber have been isolated (John et al., Proc. Natl. Acad. Sci. USA, 89:5769 (1992). cDNA clones from tomato displaying differential expression during fruit development have been isolated and characterized (Mansson et al., Gen. Genet., 200:356 (1985), Slater et al., Plant Mol. Biol., 5:137 (1985)). The promoter for polygalacturonase gene is active in fruit ripening. The polygalacturonase gene is described in U.S. Pat. No. 4,535,060, U.S. Pat. No. 4,769,061, U.S. Pat. No. 4,801,590, and U.S. Pat. No. 5,107,065, which disclosures are incorporated herein by reference.

Other examples of tissue-specific promoters include those that direct expression in leaf cells following damage to the leaf (for example, from chewing insects), in tubers (for example, patatin gene promoter), and in fiber cells (an example of a developmentally-regulated fiber cell protein is E6 (John et al., Proc. Natl. Acad. Sci. USA, 89:5769 (1992). The E6 gene is most active in fiber, although low levels of transcripts are found in leaf, ovule and flower.

The tissue-specificity of some "tissue-specific" promoters may not be absolute and may be tested by one skilled in the art using the diphtheria toxin sequence. One can also achieve tissue-specific expression with "leaky" expression by a combination of different tissue-specific promoters (Beals et al., Plant Cell, 9:1527 (1997)). Other tissue-specific promoters can be isolated by one skilled in the art (see U.S. Pat. No. 5,589,379).

Several inducible promoters have been reported. Many are described in a review by Gatz, in Current Opinion in Biotechnology, 7:168 (1996) and Gatz, C., Annu. Rev. Plant Physiol. Plant Mol. Biol., 48:89 (1997). Examples include tetracycline repressor system, Lac repressor system, copper-inducible systems, salicylate-inducible systems (such as the PR1a system), glucocorticoid-inducible (Aoyama T. et al., N—H Plant Journal, 11:605 (1997)) and ecdysone-inducible systems. Other inducible promoters include ABA- and turgor-inducible promoters, the promoter of the auxin-binding protein gene (Schwob et al., Plant J., 4:423 (1993)), the UDP glucose flavonoid glycosyl-transferase gene promoter (Ralston et al., Genetics, 119:185 (1988)), the MPI proteinase inhibitor promoter (Cordero et al., Plant J., 6:141 (1994)), and the glyceraldehyde-3-phosphate dehydrogenase gene promoter (Kohler et al., Plant Mol. Biol., 29; 1293 (1995); Quigley et al., J. Mol. Evol., 29:412 (1989); Martinez et al., J. Mol. Biol., 208:551 (1989)). Also included are the benzene sulphonamide-inducible (U.S. Pat. No. 5,364,780) and alcohol-inducible (WO 97/06269 and WO 97/06268) systems and glutathione S-transferase promoters.

Other studies have focused on genes inducibly regulated in response to environmental stress or stimuli such as increased salinity, drought, pathogen and wounding. (Graham et al., J. Biol. Chem., 260:6555 (1985); Graham et al., J. Biol. Chem., 260:6561 (1985), Smith et al., Planta, 168:94 (1986)). Accumulation of metallocarboxypeptidase-inhibitor protein has been reported in leaves of wounded potato plants (Graham et al., Biochem. Biophys. Res. Comm., 101:1164 (1981)). Other plant genes have been reported to be induced by methyl jasmonate, elicitors, heat-shock, anaerobic stress, or herbicide safeners.

Preferably, in the case of a multicellular organism, the promoter can also be specific to a particular tissue, organ or stage of development. Examples of such promoters include, but are not limited to, the *Zea mays* ADP-gpp and the *Zea mays* Gamma zein promoter and the *Zea mays* globulin promoter.

Expression of a gene in a transgenic plant may be desired only in a certain time period during the development of the plant. Developmental timing is frequently correlated with tissue specific gene expression. For example, expression of zein storage proteins is initiated in the endosperm about 15 days after pollination.

The polynucleotide sequences encoding the α-amylase enzyme of the present invention may be operably linked to polynucleotide sequences encoding localization signals or signal sequence (at the N- or C-terminus of a polypeptide), e.g., to target the hyperthermophilic enzyme to a particular compartment within a plant. Examples of such targets include, but are not limited to, the vacuole, endoplasmic reticulum, chloroplast, amyloplast, starch granule, or cell wall, or to a particular tissue, e.g., seed. The expression of a polynucleotide encoding a truncated α-amylase enzyme having a signal sequence in a plant, in particular, in conjunction with the use of a tissue-specific or inducible promoter, can yield high levels of localized α-amylase enzyme in the plant.

Numerous signal sequences are known to influence the expression or targeting of a polynucleotide to a particular compartment or outside a particular compartment. Suitable signal sequences and targeting promoters are known in the art and include, but are not limited to, those provided herein.

In one embodiment, the truncated α-amylase is targeted to the apoplast using, for example, the maize Gamma zein N-terminal signal sequence, which confers apoplast-specific targeting of proteins. Directing the enzyme to the apoplast will allow the enzyme to be localized in a manner that it will not come into contact with the substrate. In this manner the enzymatic action of the enzyme will not occur until the enzyme contacts its substrate. The enzyme can be contacted with its substrate by the process of milling (physical disruption of the cell integrity), or heating the cells or plant tissues to disrupt the physical integrity of the plant cells or organs that contain the enzyme. For example the truncated α-amylase can be targeted to the apoplast or to the endoplasmic reticulum so as not to come into contact with starch granules in the amyloplast. Milling of the grain will disrupt the integrity of the grain and the truncated α-amylase enzyme will then contact the starch granules. In this manner the potential negative effects of co-localization of an enzyme and its substrate can be circumvented.

Additionally, vectors may be constructed and employed in the intracellular targeting of a specific gene product within the cells of a transgenic plant or in directing a protein to the extracellular environment. This will generally be achieved by joining a DNA sequence encoding a transit or signal peptide sequence to the coding sequence of a particular gene. The resultant transit, or signal, peptide will transport the protein to a particular intracellular, or extracellular destination, respectively, and will then be post-translationally removed. Transit or signal peptides act by facilitating the transport of proteins through intracellular membranes, e.g., vacuole, vesicle, plastid and mitochondrial membranes, whereas signal peptides direct proteins through the extracellular membrane.

A signal sequence such as the maize Gamma zein N-terminal signal sequence for targeting to the endoplasmic reticulum and secretion into the apoplast may be operably linked to a polynucleotide encoding the truncated α-amylase enzyme in accordance with the present invention (Torrent et al., 1997). Another signal sequence is the amino acid sequence SEKDEL (SEQ ID NO:13) for retaining polypeptides in the endoplasmic reticulum (Munro and Pelham, 1987). For example, a polynucleotide encoding SEQ ID NO:6 or 8, which comprises the N-terminal signal sequence from maize Gamma zein operably linked to a truncated α-amylase enzyme which is operably linked to SEKDEL. A polypeptide may also be targeted to the amyloplast by fusion to the waxy amyloplast targeting peptide (Klosgen et al., 1986) or to a starch granule. For example, the polynucleotide encoding the truncated α-amylase may be operably linked to a chloroplast (amyloplast) transit peptide (CTP) and a starch binding domain, e.g., from the waxy gene. Moreover, the polynucleotide encoding the truncated α-amylase may be fused to target starch granules using the waxy starch binding domain.

The polynucleotides of the present invention, in addition to processing signals, may further include other regulatory sequences, as is known in the art. "Regulatory sequences" and "suitable regulatory sequences" each refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences include enhancers, promoters, translation leader sequences, introns, and polyadenylation signal sequences. They include natural and synthetic sequences as well as sequences that are a combination of synthetic and natural sequences.

A variety of transcriptional terminators are available for use in expression cassettes. These are responsible for the termination of transcription beyond the transgene and correct mRNA polyadenylation. The termination region may be native with the transcriptional initiation region, may be native with the operably linked DNA sequence of interest, may be native with the plant host, or may be derived from another source (i.e., foreign or heterologous to the promoter, the DNA sequence of interest, the plant host, or any combination thereof). Appropriate transcriptional terminators are those that are known to function in plants and include the CAMV 35S terminator, the tml terminator, the nopaline synthase terminator and the pea rbcs E9 terminator. These can be used in both monocotyledons and dicotyledons. In addition, a gene's native transcription terminator may be used.

Generally, the expression cassette will comprise a selectable marker gene for the selection of transformed cells. Selectable marker genes are utilized for the selection of transformed cells or tissues. Selectable markers may also be used in the present invention to allow for the selection of transformed plants and plant tissue, as is well-known in the art. One may desire to employ a selectable or screenable marker gene as, or in addition to, the expressible gene of interest. "Marker genes" are genes that impart a distinct phenotype to cells expressing the marker gene and thus allow such transformed cells to be distinguished from cells that do not have the marker. Such genes may encode either a selectable or screenable marker, depending on whether the marker confers a trait which one can select for by chemical means, i.e., through the use of a selective agent (e.g., a herbicide, antibiotic, or the like), or whether it is simply a trait that one can identify through observation or testing, i.e., by screening (e.g., the R-locus trait). Of course, many examples of suitable marker genes are known in the art and can be employed in the practice of the invention.

Included within the terms selectable or screenable marker genes are also genes which encode a "secretable marker" whose secretion can be detected as a means of identifying or selecting for transformed cells. Examples include markers which encode a secretable antigen that can be identified by antibody interaction, or even secretable enzymes which can be detected by their catalytic activity. Secretable proteins fall into a number of classes, including small, diffusible proteins detectable, e.g., by ELISA; small active enzymes detectable in extracellular solution (e.g., β-lactamase, phosphinothricin acetyltransferase); and proteins that are inserted or trapped in the cell wall (e.g., proteins that include a leader sequence such as that found in the expression unit of extensin or tobacco PR-S).

With regard to selectable secretable markers, the use of a gene that encodes a protein that becomes sequestered in the cell wall, and which protein includes a unique epitope is also encompassed herein. Such a secreted antigen marker would ideally employ an epitope sequence that would provide low background in plant tissue, a promoter-leader sequence that would impart efficient expression and targeting across the plasma membrane, and would produce protein that is bound in the cell wall and yet accessible to antibodies. A normally secreted wall protein modified to include a unique epitope would satisfy all such requirements.

One example of a protein suitable for modification in this manner is extensin, or hydroxyproline rich glycoprotein (HPRG). For example, the maize HPRG (Steifel et al., The Plant Cell, 2:785 (1990)) molecule is well characterized in terms of molecular biology, expression and protein structure. However, any one of a variety of extensins and/or glycine-rich wall proteins (Keller et al., EMBO Journal, 8:1309 (1989)) could be modified by the addition of an antigenic site to create a screenable marker.

Possible selectable markers for use in connection with the present invention include, but are not limited to, a neo or nptII gene (Potrykus et al., Mol. Gen. Genet., 199:183 (1985)) which codes for kanamycin resistance and can be selected for using kanamycin, G418, and the like; a bar gene which confers resistance to the herbicide phosphinothricin; a gene which encodes an altered EPSP synthase protein (Hinchee et al., Biotech., 6:915 (1988)) thus conferring glyphosate resistance; a nitrilase gene such as bxn from *Klebsiella ozaenae* which confers resistance to bromoxynil (Stalker et al., Science, 242:419 (1988)); a mutant acetolactate synthase gene (ALS) which confers resistance to imidazolinone, sulfonylurea or other ALS-inhibiting chemicals (European Patent Application 154,204, 1985); a methotrexate-resistant DHFR gene (Thillet et al., J. Biol. Chem., 263:12500 (1988)); a dalapon dehalogenase gene that confers resistance to the herbicide dalapon; a phosphomannose isomerase (PMI) gene; a mutated anthranilate synthase gene that confers resistance to 5-methyl tryptophan; the hph gene which confers resistance to the antibiotic hygromycin; or the mannose-6-phosphate isomerase gene (also referred to herein as the phosphomannose isomerase gene), which provides the ability to metabolize mannose (U.S. Pat. Nos. 5,767,378 and 5,994,629). One skilled in the art is capable of selecting a suitable selectable marker gene for use in the present invention. Where a mutant EPSP synthase gene is employed, additional benefit may be realized through the incorporation of a suitable chloroplast transit peptide, CTP (European Patent Application 0,218,571, 1987).

An illustrative embodiment of a selectable marker gene capable of being used in systems to select transformants are the genes that encode the enzyme phosphinothricin acetyltransferase, such as the bar gene from *Streptomyces hygroscopicus* or the pat gene from *Streptomyces* viridochromogenes. The enzyme phosphinothricin acetyl transferase (PAT) inactivates the active ingredient in the herbicide bialaphos, phosphinothricin (PPT). PPT inhibits glutamine synthetase, (Murakami et al., Mol. Gen. Genet., 205:42 (1986); Twell et al., Plant Physiol., 91:1270 (1989)) causing rapid accumulation of ammonia and cell death. The success in using this selective system in conjunction with monocots was particularly surprising because of the major difficulties which have been reported in transformation of cereals (Potrykus, Trends Biotech., 7:269 (1989)).

Where one desires to employ a bialaphos resistance gene in the practice of the invention, a particularly useful gene for this purpose is the bar or pat genes obtainable from species of *Streptomyces* (e.g., ATCC No. 21,705). The cloning of the bar gene has been described (Murakami et al., Mol. Gen. Genet., 205:42 (1986); Thompson et al., EMBO Journal, 6:2519 (1987)) as has the use of the bar gene in the context of plants other than monocots (De Block et al., EMBO Journal, 6:2513 (1987); De Block et al., Plant Physiol., 91:694 (1989)).

Screenable markers that may be employed include, but are not limited to, a β-glucuronidase or uidA gene (GUS) which encodes an enzyme for which various chromogenic substrates are known; an R-locus gene, which encodes a product that regulates the production of anthocyanin pigments (red color) in plant tissues (Dellaporta et al., in Chromosome Structure and Function, pp. 263-282 (1988)); a β-lactamase gene (Sutcliffe, PNAS USA, 75:3737 (1978)), which encodes an enzyme for which various chromogenic substrates are known (e.g., PADAC, a chromogenic cephalosporin); a xylE gene (Zukowsky et al., PNAS USA, 80:1101 (1983)) which encodes a catechol dioxygenase that can convert chromogenic catechols; a tyrosinase gene (Katz et al., J. Gen. Microbiol., 129:2703 (1983)) which encodes an enzyme capable of oxidizing tyrosine to DOPA and dopaquinone which in turn condenses to form the easily detectable compound melanin; a β-galactosidase gene, which encodes an enzyme for which there are chromogenic substrates; a luciferase (lux) gene (Ow et al., Science, 234:856 (1986)), which allows for bioluminescence detection; or an aequorin gene (Prasher et al., Biochem. Biophys. Res. Comm., 126:1259 (1985)), which may be employed in calcium-sensitive bioluminescence detection, or a green fluorescent protein gene (Niedz et al., Plant Cell Reports, 14: 403 (1995)).

Genes from the maize R gene complex are contemplated to be particularly useful as screenable markers. The R gene complex in maize encodes a protein that acts to regulate the production of anthocyanin pigments in most seed and plant tissue. A gene from the R gene complex is suitable for maize transformation, because the expression of this gene in transformed cells does not harm the cells. Thus, an R gene introduced into such cells will cause the expression of a red pigment and, if stably incorporated, can be visually scored as a red sector. If a maize line carries dominant allelles for genes encoding the enzymatic intermediates in the anthocyanin biosynthetic pathway (C2, A1, A2, Bz1 and Bz2), but carries a recessive allele at the R locus, transformation of any cell from that line with R will result in red pigment formation. Exemplary lines include Wisconsin 22 which contains the rg-Stadler allele and TR112, a K55 derivative which is r-g, b, P1. Alternatively any genotype of maize can be utilized if the C1 and R alleles are introduced together. A further screenable marker contemplated for use in the present invention is firefly luciferase, encoded by the lux gene. The presence of the lux gene in transformed cells may be detected using, for example, X-ray film, scintillation counting, fluorescent spectrophotometry, low-light video cameras, photon counting cameras or multiwell luminometry. It is also envisioned that this system may be developed for populational screening for bioluminescence, such as on tissue culture plates, or even for whole plant screening.

Numerous sequences have been found to enhance gene expression from within the transcriptional unit and these sequences can be used in conjunction with the genes of this invention to increase their expression in transgenic plants.

Various intron sequences have been shown to enhance expression. For example, the introns of the maize Adh1 gene have been found to significantly enhance the expression of the full length gene under its cognate promoter when introduced into maize cells. Intron 1 was found to be particularly effective and enhanced expression in fusion constructs with the chloramphenicol acetyltransferase gene (Callis et al., Genes Develop. 1: 1183-1200 (1987)). In the same experimental system, the intron from the maize bronze 1 gene had a similar effect in enhancing expression. Intron sequences have been routinely incorporated into plant transformation vectors, typically within the non-translated leader.

A number of non-translated leader sequences derived from viruses are also known to enhance expression. Specifically, leader sequences from Tobacco Mosaic Virus (TMV, the "W-sequence"), Maize Chlorotic Mottle Virus (MCMV), and Alfalfa Mosaic Virus (AMV) have been shown to be effective in enhancing expression (e.g. Gallie et al. Nucl. Acids Res. 15: 8693-8711 (1987); Skuzeski et al. Plant Molec. Biol. 15: 65-79 (1990)). Other leader sequences known in the art include but are not limited to: picornavirus leaders, for example, EMCV leader (Encephalomyocarditis 5' noncoding region) (Elroy-Stein, O., Fuerst, T. R., and Moss, B. PNAS USA 86:6126-6130 (1989)); potyvirus leaders, for example, TEV leader (Tobacco Etch Virus) (Allison et al., 1986); MDMV leader (Maize Dwarf Mosaic Virus); Virology 154: 9-20); human immunoglobulin heavy-chain binding protein (BiP) leader, (Macejak, D. G., and Samow, P., Nature 353: 90-94 (1991); untranslated leader from the coat protein mRNA of alfalfa mosaic virus (AMV RNA 4), (Jobling, S. A., and Gehrke, L., Nature 325:622-625 (1987); tobacco mosaic virus leader (TMV), (Gallie, D. R. et al., Molecular Biology of RNA, pages 237-256 (1989); and Maize Chlorotic Mottle Virus leader (MCMV) (Lommel, S. A. et al., Virology 81:382-385 (1991). See also, Della-Cioppa et al., Plant Physiology 84:965-968 (1987).

Plant Transformation

Once a nucleic acid sequence encoding the truncated amylase has been cloned into an expression system, it is transformed into a plant cell. The word "plant" refers to any plant, particularly to seed plant, and "plant cell" is a structural and physiological unit of the plant, which comprises a cell wall but may also refer to a protoplast. The plant cell may be in form of an isolated single cell or a cultured cell, or as a part of higher organized unit such as, for example, a plant tissue, or a plant organ. The term "transformation" refers to the transfer of a nucleic acid fragment into the genome of a host cell, resulting in genetically stable inheritance. Host cells containing the transformed nucleic acid fragments are referred to as "transgenic" cells, and organisms comprising transgenic cells are referred to as "transgenic organisms."

Plants useful in the present invention also include, but are not limited to, crops producing edible flowers such as cauliflower (*Brassica oleracea*), artichoke (*Cynara scolvmus*), and safflower (*Carthamus*, e.g. *tinctorius*); fruits such as apple (*Malus*, e.g. *domesticus*), banana (*Musa*, e.g. *acuminata*), berries (such as the currant, *Ribes*, e.g. *rubrum*), cherries (such as the sweet cherry, *Prunus*, e.g. *avium*), cucumber (*Cucumis*, e.g. *sativus*), grape (*Vitis*, e.g. *vinifera*), lemon (*Citrus limon*), melon (*Cucumis melo*), nuts (such as the walnut, Juglans, e.g. regia; peanut, *Arachis* hypoaeae), orange (*Citrus*, e.g. *maxima*), peach (*Prunus*, e.g. *persica*), pear (*Pyra*, e.g. *communis*), pepper (*Solanum*, e.g. *capsicum*), plum (*Prunus*, e.g. *domestica*), strawberry (*Fragaria*, e.g. *moschata*), tomato (*Lycopersicon*, e.g. *esculentum*); leafs, such as alfalfa (*Medicago*, e.g. *sativa*), sugar cane (*Saccharum*), cabbages (such as *Brassica oleracea*), endive (*Cichoreum*, e.g. *endivia*), leek (*Allium*, e.g. *porrum*), lettuce (*Lactuca*, e.g. *sativa*), spinach (*Spinacia* e.g. *oleraceae*), tobacco (*Nicotiana*, e.g. *tabacum*); roots, such as arrowroot (*Maranta*, e.g. *arundinacea*), beet (*Beta*, e.g. *vulgaris*), carrot (*Daucus*, e.g. *carota*), cassaya (*Manihot*, e.g. *esculenta*), turnip (*Brassica*, e.g. *rapa*), radish (*Raphanus*, e.g. *sativus*) yam (*Dioscorea*, e.g. *esculenta*), sweet potato (*Ipomoea batatas*); seeds, such as bean (*Phaseolus*, e.g. *vulgaris*), pea (*Pisum*, e.g. *sativum*), soybean (*Glycine*, e.g. *max*), wheat (*Triticum*, e.g. *aestivum*), barley (*Hordeum*, e.g. *vulgare*), corn (*Zea*, e.g. *mays*), rice (*Oryza*, e.g. *sativa*); grasses, such as Miscanthus grass (*Miscanthus*, e.g., *giganteus*) and switchgrass (*Panicum*, e.g. *virgatum*); trees such as poplar (*Populus*, e.g. *tremula*), pine (*Pinus*); shrubs, such as cotton (e.g., *Gossypium hirsutum*); and tubers, such as kohlrabi (*Brassica*, e.g. *oleraceae*), potato (*Solanum*, e.g. *tuberosum*), and the like.

Examples of methods of transformation of plants and plant cells include *Agrobacterium*-mediated transformation (De Blaere et al., 1987) and particle bombardment technology (Klein et al. 1987; U.S. Pat. No. 4,945,050). Whole plants may be regenerated from transgenic cells by methods well known to the skilled artisan (see, for example, Fromm et al., 1990).

The receptor and target expression cassettes of the present invention can be introduced into the plant cell in a number of art-recognized ways. The term "introducing" in the context of a polynucleotide, for example, a nucleotide encoding a truncated α-amylase, is intended to mean presenting to the plant the polynucleotide in such a manner that the polynucleotide gains access to the interior of a cell of the plant. Where more than one polynucleotide is to be introduced, these polynucleotides can be assembled as part of a single nucleotide construct, or as separate nucleotide constructs, and can be located on the same or different transformation vectors.

Accordingly, these polynucleotides can be introduced into the host cell of interest in a single transformation event, in separate transformation events, or, for example, in plants, as part of a breeding protocol. The methods of the invention do not depend on a particular method for introducing one or more polynucleotides into a plant, only that the polynucleotide(s) gains access to the interior of at least one cell of the plant. Methods for introducing polynucleotides into plants are known in the art including, but not limited to, transient transformation methods, stable transformation methods, and virus-mediated methods.

"Transient transformation" in the context of a polynucleotide is intended to mean that a polynucleotide is introduced into the plant and does not integrate into the genome of the plant.

By "stably introducing" or "stably introduced" in the context of a polynucleotide introduced into a plant is intended the introduced polynucleotide is stably incorporated into the plant genome, and thus the plant is stably transformed with the polynucleotide.

"Stable transformation" or "stably transformed" is intended to mean that a polynucleotide, for example, a nucleotide construct described herein, introduced into a plant integrates into the genome of the plant and is capable of being inherited by the progeny thereof, more particularly, by the progeny of multiple successive generations.

Numerous transformation vectors available for plant transformation are known to those of ordinary skill in the plant transformation arts, and the genes pertinent to this invention can be used in conjunction with any such vectors. The selection of vector will depend upon the preferred transformation technique and the target species for transformation. For certain target species, different antibiotic or herbicide selection markers may be preferred as discussed elsewhere herein.

Methods for regeneration of transformed plants are well known in the art. For example, Ti plasmid vectors have been utilized for the delivery of foreign DNA, as well as direct DNA uptake, liposomes, electroporation, microinjection, and microprojectiles. In addition, bacteria from the genus *Agrobacterium* can be utilized to transform plant cells. Below are descriptions of representative techniques for transforming both dicotyledonous and monocotyledonous plants, as well as a representative plastid transformation technique.

Many vectors are available for transformation using *Agrobacterium tumefaciens*. These typically carry at least one T-DNA border sequence and include vectors such as pBIN19 (Bevan, Nucl. Acids Res. (1984)). For the construction of vectors useful in *Agrobacterium* transformation, see, for example, US Patent Application Publication No. 2006/0260011, herein incorporated by reference.

Transformation without the use of *Agrobacterium tumefaciens* circumvents the requirement for T-DNA sequences in the chosen transformation vector and consequently vectors lacking these sequences can also be utilized. Transformation techniques that do not rely on *Agrobacterium* include transformation via particle bombardment, protoplast uptake (e.g. PEG and electroporation) and microinjection. The choice of vector depends largely on the preferred selection for the species being transformed. For the construction of such vectors, see, for example, US Application No. 20060260011, herein incorporated by reference.

Transformation techniques for dicotyledons are well known in the art and include *Agrobacterium*-based techniques and techniques that do not require *Agrobacterium*. Non-*Agrobacterium* techniques involve the uptake of exogenous genetic material directly by protoplasts or cells. This method can be accomplished by PEG or electroporation mediated uptake, particle bombardment-mediated delivery, or microinjection. Examples of these techniques are described by Paszkowski et al., EMBO J. 3: 2717-2722 (1984), Potrykus et al., Mol. Gen. Genet. 199: 169-177 (1985), Reich et al., Biotechnology 4: 1001-1004 (1986), and Klein et al., Nature 327: 70-73 (1987). In each case the transformed cells are regenerated to whole plants using standard techniques known in the art.

*Agrobacterium*-mediated transformation is a preferred technique for transformation of dicotyledons because of its high efficiency of transformation and its broad utility with many different species. *Agrobacterium* transformation typically involves the transfer of the binary vector carrying the foreign DNA of interest to an appropriate *Agrobacterium* strain which may depend of the complement of vir genes carried by the host *Agrobacterium* strain either on a co-resident Ti plasmid or chromosomally (Uknes et al. Plant Cell 5: 159-169 (1993)). The transfer of the recombinant binary vector to *Agrobacterium* is accomplished by a triparental mating procedure using *E. coli* carrying the recombinant binary vector, a helper *E. coli* strain which carries a plasmid that is able to mobilize the recombinant binary vector to the target *Agrobacterium* strain. Alternatively, the recombinant binary vector can be transferred to *Agrobacterium* by DNA transformation (Hofgen & Willmitzer, Nucl. Acids Res. 16: 9877 (1988)).

Transformation of the target plant species by recombinant *Agrobacterium* usually involves co-cultivation of the *Agrobacterium* with explants from the plant and follows protocols well known in the art. Transformed tissue is regenerated on selectable medium carrying the antibiotic or herbicide resistance marker present between the binary plasmid T-DNA borders.

Another approach to transforming plant cells with a gene involves propelling inert or biologically active particles at plant tissues and cells. This technique is disclosed in U.S. Pat. Nos. 4,945,050, 5,036,006, and 5,100,792. Generally, this procedure involves propelling inert or biologically active particles at the cells under conditions effective to penetrate the outer surface of the cell and afford incorporation within the interior thereof. When inert particles are utilized, the vector can be introduced into the cell by coating the particles with the vector containing the desired gene. Alternatively, the target cell can be surrounded by the vector so that the vector is carried into the cell by the wake of the particle. Biologically active particles (e.g., dried yeast cells, dried bacterium or a bacteriophage, each containing DNA sought to be introduced) can also be propelled into plant cell tissue.

Transformation of most monocotyledon species has now also become routine. Preferred techniques include direct gene transfer into protoplasts using PEG or electroporation techniques, and particle bombardment into callus tissue. Transformations can be undertaken with a single DNA species or multiple DNA species (i.e. co-transformation) and both of these techniques are suitable for use with this invention. Co-transformation may have the advantage of avoiding complete vector construction and of generating transgenic plants with unlinked loci for the gene of interest and the selectable marker, enabling the removal of the selectable marker in subsequent generations, should this be regarded desirable.

Patent Applications EP 0 292 435, EP 0 392 225, and WO 93/07278 describe techniques for the preparation of callus and protoplasts from an elite inbred line of maize, transformation of protoplasts using PEG or electroporation, and the regeneration of maize plants from transformed protoplasts. Gordon-Kamm et al. (*Plant Cell* 2: 603-618 (1990)) and Fromm et al. (*Biotechnology* 8: 833-839 (1990)) have published techniques for transformation of A188-derived maize line using particle bombardment. Furthermore, WO 93/07278 and Koziel et al. (*Biotechnology* 11: 194-200 (1993)) describe techniques for the transformation of elite inbred lines of maize by particle bombardment. This technique utilizes immature maize embryos of 1.5-2.5 mm length excised from a maize ear 14-15 days after pollination and a PDS-1000He Biolistics device for bombardment.

The plants obtained via transformation with a nucleic acid sequence of the present invention can be any of a wide variety of plant species, including those of monocots and dicots; however, the plants used in the method of the invention are preferably selected from the list of agronomically important target crops set forth supra. The expression of a gene of the present invention in combination with other characteristics important for production and quality can be incorporated into plant lines through breeding. Breeding approaches and techniques are known in the art. See, for example, Welsh J. R., Fundamentals of Plant Genetics and Breeding, John Wiley & Sons, NY (1981); Crop Breeding, Wood D. R. (Ed.) American Society of Agronomy Madison, Wis. (1983); Mayo O., The Theory of Plant Breeding, Second Edition, Clarendon Press, Oxford (1987); Singh, D. P., Breeding for Resistance to Diseases and Insect Pests, Springer-Verlag, NY (1986); and Wricke and Weber, Quantitative Genetics and Selection Plant Breeding, Walter de Gruyter and Co., Berlin (1986).

The genetic properties engineered into the transgenic seeds and plants described above are passed on by sexual reproduction or vegetative growth and can thus be maintained and propagated in progeny plants. Generally, maintenance and propagation make use of known agricultural methods developed to fit specific purposes such as tilling, sowing or harvesting.

The following examples are offered by way of illustration and not by way of limitation.

EXPERIMENTAL EXAMPLES

Example 1

Specific Activity of Purified Amylase in Transgenic Plants

Constructs. Three constructs were generated for the purpose of expressing three forms of barley alpha-amylase in transgenic corn grain. All three constructs contained the maize gamma zein promoter which is an endosperm tissue preferred promoter, a barley alpha amylase gene (full length or truncated), an ER retention sequence, an intron from phosphoenolpyruvate carboxylase (PEPC) and the 35S terminator from cauliflower mosaic virus.

Construct pBASIC11680 contained a gene encoding the mature barley alpha-amylase AmyI protein. Construct pBASIC15746 contained a gene encoding the barley alpha-amylase AmyI protein with two N-terminal amino acids, MA, removed and nine C-terminal amino acids, GAAATLQRS, removed as well. Construct pBASIC 15747 contained a gene encoding the barley alpha-amylase AmyI protein with two N-terminal amino acids, MA, removed and ten C-terminal amino acids, NGAAATLQRS, were removed.

Seeds. T1 seeds from several events generated using vectors pBASIC 11680, 15746, and 15747 were selected and pooled for purification of full length AmyI, AmyIΔ9, and AmyIΔ10, respectively. Construct 15746 corresponds to SEQ ID NO:5 and construct 15747 corresponds to SEQ ID NO:7. The full length AmyI sequence is set forth in SEQ ID NO:9.

Reagents. Epoxy activated-Sepharose 6B was purchased from Sigma (cat #E6754). β-cyclodextrin (cycloheptaamylose) was purchased from Sigma (cat #C-4767). Ceralpha HR reagent was purchased from Megazyme (ICC Standard No. 303).

Preparation of β-cyclodextrin affinity column. The β-cyclodextrin affinity resin was prepared with a protocol modified from Reference 1 and Reference 2. A detailed protocol is described below. The protocol allows one to prepare 2 parallel batches, 4 g of dry resin was used for each batch.

1. Weigh 4 g (×2) Epoxy activated Sepharose 6B powder. Swell the resin in 50 ml distilled water, pour the resin into a Bio-Rad column (2.5 cm OD) and wash with 200 ml distilled water.
2. Prepare a solution of 4 g β-cyclodextrin in 50 ml 0.1 N NaOH.
3. Transfer the resins from step 1 to 50 ml conical tubes (2 tubes) and centrifuge at 750 g for 2 min. Pipet away the excess water (about 13 ml resin each tube).

4. Add 24 ml β-cyclodextrin solution from step 2 to each tube with the resins and incubate at 30 degrees C. warm room for 24 hours with slow rotation mixing for efficient coupling.
5. Pour the resins onto a 600 ml glass filtered funnel and wash with 2 L of water. Then wash with 1 L of 25 mg/ml D-glucose solution to block any remaining active groups. Wash with 1 L water again.
6. Wash the coupled resins with 3 cycles of 100 ml alternating pH buffers. Buffer A: 0.1 M Tris-HCl pH 8, 0.5 M NaCl; Buffer B: 0.1 M NaOAc pH 4.5, 0.5 M NaCl.
7. Wash with 300 ml of 20 mM NaOAc, pH 5.2, 2.5 mM $CaCl_2$ buffer.
8. Transfer and combine the resins to a 50 ml tube, add 20 mM NaOAc, pH 5.2, 2.5 mM $CaCl_2$ storage buffers to a total volume of about 40 ml. Store the coupled resins at 4° C. The total amount of coupled resins is about 24 ml.

Protein extraction and purification. T1 seeds of full length AmyI (pBASIC11680), AmyIΔ9 (pBASIC15746) and AmyIΔ10 (pBASIC15747) were ground in parallel with KLECO Grinder for 45 seconds. 10.2 g of full length AmyI-containing corn flour, 12.2 g of AmyIΔ9-containing corn flour, and 10.2 g of AmyIΔ10-containing corn flour were suspended in 200 ml extraction buffer (20 mM NaOAc, 2.5 mM $CaCl_2$, pH 5.2) and stirred at room temperature for 5 min. The slurries were homogenized with a Polytron (Brinkmann Homogenizer, Model PT 10/35) for 20 sec with power level set at 9 and transferred into 250 ml centrifuge bottles and incubated at 38° C. in a water bath for 45 min. The samples were then centrifuged at 4,500 rpm for 10 min with a Sorvall GS3 rotor. The supernatants were filtered with 0.45 μM Millipore Nylon HNWP 47 mm membrane filter. The filtrates were then mixed with 3 ml β-cyclodextrin affinity resin (6 ml 50% resin) each in 250 ml bottles and were slowly rotated at 4° C. for over night. The mixtures were transferred into 3×22 cm Bio-Rad columns and washed with 100 ml of 20 mM NaOAc, 2.5 mM $CaCl_2$, pH 5.2 buffer for each sample. The AmyI and mutant proteins were then eluted with 20 mM NaOAc, 2.5 mM $CaCl_2$, pH 5.2 buffer containing 5 mg/ml (4.4 mM) β-cyclodextrin for 6 times with 10 ml elution buffer each time. The eluted samples of each protein were pooled and concentrated with Amicon centricon Plus 20 (10,000 MW cut off) at 4,000 rpm for 10 min at 8° C. The concentrated samples were buffer-exchanged with 20 mM NaOAc, 2.5 mM $CaCl_2$, pH 5.2 buffer until the β-cyclodextrin concentrations were reduced by more than 10,000 fold (estimated from dilution factors) in the Amicon centricon Plus 20. The concentrated and buffer exchanged samples were stored at 4° C.

SDS-PAGE analysis and protein quantification. Various amounts of the purified enzymes were analyzed on 4-12% Bis-Tris SDS-PAGE gel with XT MOPS buffer from BioRad by following the manufacturer's instructions. The protein concentrations were quantified with PIERCE Coomassie Plus reagent using BSA as standards. 10 μL of diluted samples or standards were mixed with 300 μL Coomassie Plus reagents and the absorbance at 595 nM was read in a plate reader with path check set to the ON position. The dilution factors were 3 fold for full length AmyI, 8 fold for AmyIΔ9, and 8 fold for AmyIΔ10. The absorbance readings were in the optimal linear range of 0.5-1.1.

Activity assay. The activity of the purified corn-expressed full length AmyI and truncation mutants was assayed using a modified Megazyme Ceralpha method. The enzymes were diluted to 0.025 μg/ml in 100 mM NaOAc, pH 5.5 buffer with 1 mg/ml BSA and incubated with the Ceralpha reagent at 40° C. for 20 min in a thermocylcer (PE Geneamp PCR system 9700). The reactions were stopped with 1% $Na_3PO_4$ and absorbance at 400 nm was taken. The $A_{400}$ readings were ensured to be within the optimal range of 0.5 to 1.0. Four duplicates of assays were run on two separate days for each enzyme. One unit is defined as the amount of enzyme (in the presence of excess thermostable α-glucosidase) required to release one micromole of p-nitrophenol in one minute under the defined assay conditions.

Results

The purified full length AmyI and truncation mutants were analyzed on 4-12% Bis-Tris SDS-PAGE gel with XT MOPS buffer. The proteins were purified to close to homogeneity and migrated between 51 KDa and 39 KDa protein standards (based on the apparent molecular weights of Invitrogen See Blue Plus2 prestained molecular weight standards with NuPAGE MOPS buffer). The theoretical molecular weights for full length AmyI, AmyIΔ9, and AmyIΔ10 with the C-terminal SEKDEL (SEQ. ID NO: 13) sequence and without N-terminal signal peptide sequence were 46.3 KDa, 45.3 KDa, and 45.1 KDa, respectively.

The protein concentrations were 1.18 mg/ml for full length AmyI, 5.09 mg/ml for AmyIΔ9, and 4.19 mg/ml for AmyIΔ10. The total amount of purified protein recovered from 10 g seeds was 0.56 mg for full length AmyI, 1.67 mg for AmyIΔ9, and 2.75 mg for AmyIΔ10 (Table 1).

The activity of the purified full length AmyI and the truncation mutants were assayed with a modified Megazyme Ceralpha method (Table 1).

TABLE 1

Specific activities and purification yields of Corn Barley AmyI and truncated mutants

| Enzyme | Specific activity (U/mg) | $k_{cat}$ ($sec^{-1}$) |
|---|---|---|
| full length | 1010 ± 40 | 0.36 |
| AmyIΔ9 | 1420 ± 80 | 0.52 |
| AmyIΔ10 | 1270 ± 140 | 0.47 |

One unit is defined as the amount of enzyme (in the presence of excess thermostable α-glucosidase) required to release one micromole of p-nitrophenol in one minute at 40° C. in 100 mM NaOAc, pH 5.5 buffer with 1 mg/ml BSA.

The specific activity data generated in table 1 indicates that the specific activity of the truncated alpha-amylase enzymes is substantially similar to the specific activity of the full length enzyme.

Example 2

Evaluation of Events Expressing Alpha-Amylase without Purification of the Amylase Sample Preparation from Individual Events:

For full length AmyI, T1 seeds from 121 events were pooled together to generate a single sample of transgenic corn. Taqman analysis of the individual events indicated that each event contained 1 or more copies of the amylase gene. Pooled seeds were ground to a flour for 45 seconds in a Kleco grinding vessel (Kinetic Laboratory Equipment Company) containing a steel ball. Flour was weighed and then transferred to a 15 mL conical tube.

For AmyIΔ9 and AmyIΔ10, 20 T1 seed from each event were ground independently as described above. There were 19 AmyIΔ9 events and 21 AmyIΔ10 events.

Total Protein Extraction from Maize Flour:
1. Add 3 mL of extraction buffer (20 mM NaOAc, 2.5 mM $CaCl_2$, pH 5.2) to the samples.
2. Seal the tubes with caps using a hammer.

3. Shake vigorously until the flour is suspended in the buffer.
4. Rotate at room temperature on a Rugged Rotator (Glas-Col) at 70% for 5 minutes.
5. Incubate at 40 degrees C. in a water bath for 30 minutes.
6. Rotate the samples for another 5 minutes at room temperature after incubation. Centrifuge the samples at 3000 rpm for 5 minutes.

Activity Assay:

Alpha amylase activity was measured in the above samples using a Ceralpha HR assay adapted from Application group Ceralpha HR assay method SOP (Feb. 1, 2005), and Megazyme *ALPHA-AMYLASE assay procedure (Ceralpha Method) using Amylase HR Reagent*, ICC Standard No. 303. One Ceralpha Unit of α-Amylase activity is defined as the amount of enzyme, in the presence of excess thermostable α-glucosidase, required to release one micromole of p-nitrophenol in one minute under the defined assay conditions. Our assay condition is at pH 5.5 (100 mM NaOAc, pH 5.5 buffer with 1 mg/ml BSA), 60° C. Note that the activity calculated is a Ceralpha unit. According to Megzyme, 1 mM PNP in 1% tri-sodium phosphate gives absorbance 18.1 at 400 nm. So 1M of PNP in tri-sodium phosphate gives absorbance 18,100 at 400 nm. The following calculations were used to determine alpha-amylase activity in the extracted flour samples:

$\Delta A_{400}/18,100 = [PNP]$ (mol/l or M) in the final plate.

[PNP] in plate (mol/l×8×100×10$^{-6}$1×1×10$^6$ (μmol/mol)=PNP (μmol/*rxn*)

PNP (μmol/*rxn*)/(0.05 ml×20 min)=units/ml of diluted α-Amylase units/ml in diluted enzyme× dilution=Ceralpha Units/ml in α-Amylase sample Or $\Delta A_{400}$×0.0442×dilution of enzyme=Ceralpha U/ml in α-Amylase sample The Ceralpha HR assay method was:
1. Dilute samples in dilution buffer (100 mM NaOAc, pH 5.5 buffer with 5 mM CaCl$_2$, 1 mg/ml BSA) to get an assay in the range of 0.5 to 1.5 OD$_{400}$.
2. Turn on the Thermocylcer (GeneAmp).
3. In a PCR plate add 50 μl of each diluted Amylase sample.
4. Add 175 μl of Stop solution (11% of Na$_3$PO$_4$ (Fisher)) to each well of a microtiter plate. There should be two wells of Stop solution for each sample assayed.
5. Mix 50 μl of substrate (Ceralpha HR reagent from Megazyme) with the sample. Pipette 3 times with swirling. Prepare substrate as indicated in the instructions from Megazyme (10 ml water/bottle).
6. Immediately, remove 25 μl of the mixture and mix with 175 μl of Stop solution. Pipette 3 times with swirling. This is the 0-time point.
7. Place plate in the thermocycler which is already at 60° C. and start the timer. Incubate the PCR plate for 20 min at 60° C.
8. After 20 min. immediately remove the plate and place it in a cold block.
9. Remove 25 μl of product and mix with 175 μl of Stop solution in another microtiter plate. This is the 20 min. time point.
10. Read OD$_{400}$ in the plate reader. Set Pathcheck to ON (this will normalize the sample absorbance reading as pathlength 1 cm).

Calculate $\Delta A_{400}$, the change in A$_{400}$ between the 0 and 20 min point.

Table 2 describes the alpha-amylase activity detected in ground corn flour without purification of the enzyme. As outlined in Example 1, the truncated alpha-amylase enzymes did not show an appreciable difference in specific activity as compared to the full length AmyI enzyme. Full length AmyI analysis is based upon the pooled sample. AmyIΔ9 and AmyIΔ10 analyses are based upon an average of the independent event results. The results, as outlined in Table 2, demonstrate that plants expressing the truncated alpha-amylase enzymes accumulate more enzyme than the plants expressing the full length alpha-amylase as the enzyme activity in these events is significantly greater than the enzyme activity observed in plants expressing the full length AmyI enzyme. The difference in enzyme activity in the transgenic plants was attributed to increased enzyme accumulation as it was previously demonstrated that the truncated enzyme is not more active than the full length enzyme.

TABLE 2

| | Pooled event evaluation | | | | | |
|---|---|---|---|---|---|---|
| Enzyme | Total events | Average seed weight (g/kernel) | Average activity per gram (U/g) | Average activity per kernel (U/kernel) | Activity increase compared to full length (gram basis) | Activity increase compared to full length (kernel basis) |
| Full length | 121 | 0.153 | 348.2 | 53 | NA | NA |
| AmyIΔ9 | 19 | 0.168 | 954.9 | 161 | 2.7 | 3.0 |
| AmyIΔ10 | 21 | 0.138 | 873.6 | 121 | 2.5 | 2.3 |

REFERENCES

1. Vretblad P. (1974) "Immobilization of ligands for biospecific affinity chromatography via their hydroxyl groups. The cyclohexaamylose-beta-amylase system." FEBS letters 47: 86-89.
2. Silvanovich M. P. and Hill R. D. (1976) "Affinity chromatography of cereal α-amylase"Analytical Biochem 73: 430-433.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A plant cell that has been stably transformed with an expression cassette comprising a polynucleotide encoding a truncated α-amylase, wherein said polynucleotide is selected from the group consisting of:
   a) the nucleotide sequence set forth in SEQ ID NO:1 or 3;
   b) a nucleotide sequence encoding the amino acid sequence set forth in SEQ ID NO: 2 or 4, wherein said nucleotide sequence encodes a biologically-active truncated α-amylase, wherein the truncated α-amylase has increased α-amylase accumulation or secretion compared to the full-length α-amylase.

2. The plant cell of claim 1, wherein said expression cassette further comprises a promoter operably linked to said polynucleotide encoding the truncated α-amylase.

3. The plant cell of claim 2, wherein said promoter is an inducible promoter, a tissue-specific promoter, or an endosperm-specific promoter.

4. The plant cell of claim 3, wherein said endosperm-specific promoter is a maize gamma zein promoter.

5. The plant cell of claim 1, wherein said expression cassette further comprises a signal sequence operably linked to said polynucleotide encoding the truncated α-amylase.

6. The plant cell of claim 5, wherein said signal sequence targets the operably linked polypeptide encoded by the polynucleotide to a vacuole, endoplasmic reticulum (ER), chloroplast, starch granule, or cell wall of the plant cell.

7. The plant cell of claim 5, wherein said signal sequence is an ER retention sequence.

8. The plant cell of claim 5, wherein the signal sequence is an N-terminal signal sequence from gamma zein.

9. The plant cell of claim 1, wherein said plant cell is a maize cell.

10. A plant comprising the plant cell of claim 1.

11. The plant of claim 10, wherein said plant is a monocot.

12. The plant of claim 11, wherein said plant is maize.

13. A seed derived from the plant of claim 10, wherein said seed comprises the expression cassette.

14. A method for accumulating alpha-amylase in a plant comprising introducing into said plant an expression cassette comprising a polynucleotide encoding a truncated α-amylase; wherein said polynucleotide is selected from the group consisting of:

a) the nucleotide sequence set forth in SEQ ID NO:1 or 3;
b) a nucleotide sequence encoding the amino acid sequence set forth in SEQ ID NO:2 or 4, wherein said nucleotide sequence encodes a biologically-active truncated α-amylase; wherein said expression cassette further comprises a promoter that drives expression in a cell of said plant, wherein said promoter is operably linked to the polynucleotide encoding the truncated α-amylase, wherein the truncated α-amylase has increased α-amylase accumulation or secretion compared to the full-length α-amylase.

15. The method of claim 14, wherein said promoter is an inducible promoter, a tissue-specific promoter, or an endosperm-specific promoter.

16. The method of claim 15, wherein said endosperm-specific promoter is a maize gamma zein promoter.

17. The method of claim 14, further comprising a nucleotide sequence encoding a signal sequence operably linked to said polynucleotide encoding the truncated α-amylase.

18. The method of claim 17, wherein said signal sequence targets the operably linked polypeptide encoded by said polynucleotide to a vacuole, endoplasmic reticulum, chloroplast, starch granule, seed or cell wall of a plant.

19. The method of claim 18, wherein the signal sequence is an N-terminal signal sequence from gamma zein.

20. The method of claim 17, wherein the signal sequence is an ER retention sequence.

* * * * *

SEQUENCE LISTING

<160> NUMBER OF SEQ ID NOS: 13

<210> SEQ ID NO 1
<211> LENGTH: 1215
<212> TYPE: DNA
<213> ORGANISM: Hordeum vulgare
<220> FEATURE:
<221> NAME/KEY: CDS
<222> LOCATION: (1)...(1215)
<223> OTHER INFORMATION: Truncated alpha-amylase (Amy1.delta.9)

<400> SEQUENCE: 1

```
cac caa gtc ctc ttt cag ggg ttc aac tgg gag tcg tgg aag cag agc       48
His Gln Val Leu Phe Gln Gly Phe Asn Trp Glu Ser Trp Lys Gln Ser
 1               5                   10                  15 ggc ggg tgg tac aac atg atg atg ggc aag gtc gac gac atc gcc gct       96
Gly Gly Trp Tyr Asn Met Met Met Gly Lys Val Asp Asp Ile Ala Ala
             20                  25                  30 gcc gga gtc acc cac gtc tgg ctg cca ccg tcg cac tcc gtc tcc          144
Ala Gly Val Thr His Val Trp Leu Pro Pro Ser His Ser Val Ser
         35                  40                  45 aac gaa ggt tac atg cct ggt cgg ctg tac gac atc gac gcg tcc aag      192
Asn Glu Gly Tyr Met Pro Gly Arg Leu Tyr Asp Ile Asp Ala Ser Lys
     50                  55                  60 tac ggc aac gcg gcg gag ctc aag tcg ctc atc ggc gcg ctc cac ggc      240
Tyr Gly Asn Ala Ala Glu Leu Lys Ser Leu Ile Gly Ala Leu His Gly
 65                  70                  75                  80 aag ggc gtg cag gcc atc gcc gac atc gtc atc aac cac cgc tgc gcc      288
Lys Gly Val Gln Ala Ile Ala Asp Ile Val Ile Asn His Arg Cys Ala
                 85                  90                  95 gac tac aag gat agc cgc ggc atc tac tgc atc ttc gag ggc ggc acc      336
Asp Tyr Lys Asp Ser Arg Gly Ile Tyr Cys Ile Phe Glu Gly Gly Thr
            100                 105                 110 tcc gac ggc cgc ctc gac tgg ggc ccc cac atg atc tgt cgc gac gac      384
Ser Asp Gly Arg Leu Asp Trp Gly Pro His Met Ile Cys Arg Asp Asp
        115                 120                 125 acc aaa tac tcc gat ggc acc gca aac ctc gac acc gga gcc gac ttc      432
Thr Lys Tyr Ser Asp Gly Thr Ala Asn Leu Asp Thr Gly Ala Asp Phe
    130                 135                 140 gcc gcc gcg ccc gac atc gac cac ctc aac gac cgg gtc cag cgc gag      480
Ala Ala Ala Pro Asp Ile Asp His Leu Asn Asp Arg Val Gln Arg Glu
145                 150                 155                 160 ctc aag gag tgg ctc ctc tgg ctc aag agc gac ctc ggc ttc gac gcg      528
Leu Lys Glu Trp Leu Leu Trp Leu Lys Ser Asp Leu Gly Phe Asp Ala
                165                 170                 175 tgg cgc ctt gac ttc gcc agg ggc tac tcg ccg gag atg gcc aag gtg      576
Trp Arg Leu Asp Phe Ala Arg Gly Tyr Ser Pro Glu Met Ala Lys Val
            180                 185                 190 tac atc gac ggc aca tcc ccg agc ctc gcc gtg gcc gag gtg tgg gac      624
Tyr Ile Asp Gly Thr Ser Pro Ser Leu Ala Val Ala Glu Val Trp Asp
        195                 200                 205 aat atg gcc acc ggc ggc gac ggc aag ccc aac tac gac cag gac gcg      672
Asn Met Ala Thr Gly Gly Asp Gly Lys Pro Asn Tyr Asp Gln Asp Ala
    210                 215                 220 cac cgg cag aat ctg gtg aac tgg gtg gac aag gtg ggc ggc gcg gcc      720
His Arg Gln Asn Leu Val Asn Trp Val Asp Lys Val Gly Gly Ala Ala
225                 230                 235                 240 tcg gca ggc atg gtg ttc gac ttc acg acc aaa ggg ata ctg aac gct      768
Ser Ala Gly Met Val Phe Asp Phe Thr Thr Lys Gly Ile Leu Asn Ala
                245                 250                 255
```

```
                                                          -continued
gcc gtg gag ggc gag ctg tgg agg ctg atc gac ccg cag ggg aag gcc         816
Ala Val Glu Gly Glu Leu Trp Arg Leu Ile Asp Pro Gln Gly Lys Ala
        260                 265                 270 ccc ggc gtg atg gga tgg tgg ccg gcc aag gcc gtc acc ttc gtc gac         864
Pro Gly Val Met Gly Trp Trp Pro Ala Lys Ala Val Thr Phe Val Asp
    275                 280                 285 aac cac gat aca ggc tcc acg cag gcc atg tgg cca ttc ccc tcc gac         912
Asn His Asp Thr Gly Ser Thr Gln Ala Met Trp Pro Phe Pro Ser Asp
290                 295                 300 aag gtc atg cag ggc tac gcg tac atc ctc acc cac ccc ggc atc cca         960
Lys Val Met Gln Gly Tyr Ala Tyr Ile Leu Thr His Pro Gly Ile Pro
305                 310                 315                 320 tgc atc ttc tac gac cat ttc ttc aac tgg ggg ttt aag gac cag atc        1008
Cys Ile Phe Tyr Asp His Phe Phe Asn Trp Gly Phe Lys Asp Gln Ile
            325                 330                 335 gcg gcg ctg gtg gcg atc agg aag cgc aac ggc atc acg gcg acg agc        1056
Ala Ala Leu Val Ala Ile Arg Lys Arg Asn Gly Ile Thr Ala Thr Ser
        340                 345                 350 gct ctg aag atc ctc atg cac gaa gga gat gcc tac gtc gcc gag ata        1104
Ala Leu Lys Ile Leu Met His Glu Gly Asp Ala Tyr Val Ala Glu Ile
    355                 360                 365 gac ggc aag gtg gtg gtg aag atc ggg tcc agg tac gac gtc ggg gcg        1152
Asp Gly Lys Val Val Val Lys Ile Gly Ser Arg Tyr Asp Val Gly Ala
370                 375                 380 gtg atc ccg gcc ggg ttc gtg acc tcg gca cac ggc aac gac tac gcc        1200
Val Ile Pro Ala Gly Phe Val Thr Ser Ala His Gly Asn Asp Tyr Ala
385                 390                 395                 400 gtc tgg gag aag aac                                                    1215
Val Trp Glu Lys Asn
            405

<210> SEQ ID NO 2
<211> LENGTH: 405
<212> TYPE: PRT
<213> ORGANISM: Artificial Sequence
<220> FEATURE:
<223> OTHER INFORMATION: Truncated alpha-amylase (Amy1.delta.9)

<400> SEQUENCE: 2

His Gln Val Leu Phe Gln Gly Phe Asn Trp Glu Ser Trp Lys Gln Ser
 1               5                  10                  15

Gly Gly Trp Tyr Asn Met Met Met Gly Lys Val Asp Asp Ile Ala Ala
            20                  25                  30

Ala Gly Val Thr His Val Trp Leu Pro Pro Pro Ser His Ser Val Ser
        35                  40                  45

Asn Glu Gly Tyr Met Pro Gly Arg Leu Tyr Asp Ile Asp Ala Ser Lys
    50                  55                  60

Tyr Gly Asn Ala Ala Glu Leu Lys Ser Leu Ile Gly Ala Leu His Gly
65                  70                  75                  80

Lys Gly Val Gln Ala Ile Ala Asp Ile Val Ile Asn His Arg Cys Ala
                85                  90                  95

Asp Tyr Lys Asp Ser Arg Gly Ile Tyr Cys Ile Phe Glu Gly Gly Thr
            100                 105                 110

Ser Asp Gly Arg Leu Asp Trp Gly Pro His Met Ile Cys Arg Asp Asp
        115                 120                 125

Thr Lys Tyr Ser Asp Gly Thr Ala Asn Leu Asp Thr Gly Ala Asp Phe
    130                 135                 140

Ala Ala Ala Pro Asp Ile Asp His Leu Asn Asp Arg Val Gln Arg Glu
145                 150                 155                 160
```

```
Leu Lys Glu Trp Leu Leu Trp Leu Lys Ser Asp Leu Gly Phe Asp Ala
                165                 170                 175
Trp Arg Leu Asp Phe Ala Arg Gly Tyr Ser Pro Glu Met Ala Lys Val
            180                 185                 190
Tyr Ile Asp Gly Thr Ser Pro Ser Leu Ala Val Ala Glu Val Trp Asp
        195                 200                 205
Asn Met Ala Thr Gly Asp Gly Lys Pro Asn Tyr Asp Gln Asp Ala
    210                 215                 220
His Arg Gln Asn Leu Val Asn Trp Val Asp Lys Val Gly Ala Ala
225                 230                 235                 240
Ser Ala Gly Met Val Phe Asp Phe Thr Thr Lys Gly Ile Leu Asn Ala
                245                 250                 255
Ala Val Glu Gly Glu Leu Trp Arg Leu Ile Asp Pro Gln Gly Lys Ala
            260                 265                 270
Pro Gly Val Met Gly Trp Trp Pro Ala Lys Ala Val Thr Phe Val Asp
        275                 280                 285
Asn His Asp Thr Gly Ser Thr Gln Ala Met Trp Pro Phe Pro Ser Asp
    290                 295                 300
Lys Val Met Gln Gly Tyr Ala Tyr Ile Leu Thr His Pro Gly Ile Pro
305                 310                 315                 320
Cys Ile Phe Tyr Asp His Phe Phe Asn Trp Gly Phe Lys Asp Gln Ile
                325                 330                 335
Ala Ala Leu Val Ala Ile Arg Lys Arg Asn Gly Ile Thr Ala Thr Ser
            340                 345                 350
Ala Leu Lys Ile Leu Met His Glu Gly Asp Ala Tyr Val Ala Glu Ile
        355                 360                 365
Asp Gly Lys Val Val Lys Ile Gly Ser Arg Tyr Asp Val Gly Ala
    370                 375                 380
Val Ile Pro Ala Gly Phe Val Thr Ser Ala His Gly Asn Asp Tyr Ala
385                 390                 395                 400
Val Trp Glu Lys Asn
                405

<210> SEQ ID NO 3
<211> LENGTH: 1212
<212> TYPE: DNA
<213> ORGANISM: Artificial Sequence
<220> FEATURE:
<223> OTHER INFORMATION: Truncated alpha-amylase (Amy1.delta.10)
<221> NAME/KEY: CDS
<222> LOCATION: (1)...(1212)

<400> SEQUENCE: 3 cac caa gtc ctc ttt cag ggg ttc aac tgg gag tcg tgg aag cag agc      48
His Gln Val Leu Phe Gln Gly Phe Asn Trp Glu Ser Trp Lys Gln Ser
  1               5                  10                  15 ggc ggg tgg tac aac atg atg atg ggc aag gtc gac gac atc gcc gct      96
Gly Gly Trp Tyr Asn Met Met Met Gly Lys Val Asp Asp Ile Ala Ala
                 20                  25                  30 gcc gga gtc acc cac gtc tgg ctg cca ccg ccg tcg cac tcc gtc tcc     144
Ala Gly Val Thr His Val Trp Leu Pro Pro Pro Ser His Ser Val Ser
             35                  40                  45 aac gaa ggt tac atg cct ggt cgg ctg tac gac atc gac gcg tcc aag     192
Asn Glu Gly Tyr Met Pro Gly Arg Leu Tyr Asp Ile Asp Ala Ser Lys
         50                  55                  60 tac ggc aac gcg gcg gag ctc aag tcg ctc atc ggc gcg ctc cac ggc     240
Tyr Gly Asn Ala Ala Glu Leu Lys Ser Leu Ile Gly Ala Leu His Gly
 65                  70                  75                  80
```

```
aag ggc gtg cag gcc atc gcc gac atc gtc atc aac cac cgc tgc gcc      288
Lys Gly Val Gln Ala Ile Ala Asp Ile Val Ile Asn His Arg Cys Ala
            85                  90                  95 gac tac aag gat agc cgc ggc atc tac tgc atc ttc gag ggc ggc acc      336
Asp Tyr Lys Asp Ser Arg Gly Ile Tyr Cys Ile Phe Glu Gly Gly Thr
       100                 105                 110 tcc gac ggc cgc ctc gac tgg ggc ccc cac atg atc tgt cgc gac gac      384
Ser Asp Gly Arg Leu Asp Trp Gly Pro His Met Ile Cys Arg Asp Asp
           115                 120                 125 acc aaa tac tcc gat ggc acc gca aac ctc gac acc gga gcc gac ttc      432
Thr Lys Tyr Ser Asp Gly Thr Ala Asn Leu Asp Thr Gly Ala Asp Phe
       130                 135                 140 gcc gcc gcg ccc gac atc gac cac ctc aac gac cgg gtc cag cgc gag      480
Ala Ala Ala Pro Asp Ile Asp His Leu Asn Asp Arg Val Gln Arg Glu
145                 150                 155                 160 ctc aag gag tgg ctc ctc tgg ctc aag agc gac ctc ggc ttc gac gcg      528
Leu Lys Glu Trp Leu Leu Trp Leu Lys Ser Asp Leu Gly Phe Asp Ala
                165                 170                 175 tgg cgc ctt gac ttc gcc agg ggc tac tcg ccg gag atg gcc aag gtg      576
Trp Arg Leu Asp Phe Ala Arg Gly Tyr Ser Pro Glu Met Ala Lys Val
            180                 185                 190 tac atc gac ggc aca tcc ccg agc ctc gcc gtg gcc gag gtg tgg gac      624
Tyr Ile Asp Gly Thr Ser Pro Ser Leu Ala Val Ala Glu Val Trp Asp
        195                 200                 205 aat atg gcc acc ggc ggc gac ggc aag ccc aac tac gac cag gac gcg      672
Asn Met Ala Thr Gly Gly Asp Gly Lys Pro Asn Tyr Asp Gln Asp Ala
    210                 215                 220 cac cgg cag aat ctg gtg aac tgg gtg gac aag gtg ggc ggc gcg gcc      720
His Arg Gln Asn Leu Val Asn Trp Val Asp Lys Val Gly Gly Ala Ala
225                 230                 235                 240 tcg gca ggc atg gtg ttc gac ttc acg acc aaa ggg ata ctg aac gct      768
Ser Ala Gly Met Val Phe Asp Phe Thr Thr Lys Gly Ile Leu Asn Ala
                245                 250                 255 gcc gtg gag ggc gag ctg tgg agg ctg atc gac ccg cag ggg aag gcc      816
Ala Val Glu Gly Glu Leu Trp Arg Leu Ile Asp Pro Gln Gly Lys Ala
            260                 265                 270 ccc ggc gtg atg gga tgg tgg ccg gcc aag gcc gtc acc ttc gtc gac      864
Pro Gly Val Met Gly Trp Trp Pro Ala Lys Ala Val Thr Phe Val Asp
        275                 280                 285 aac cac gat aca ggc tcc acg cag gcc atg tgg cca ttc ccc tcc gac      912
Asn His Asp Thr Gly Ser Thr Gln Ala Met Trp Pro Phe Pro Ser Asp
    290                 295                 300 aag gtc atg cag ggc tac gcg tac atc ctc acc cac ccc ggc atc cca      960
Lys Val Met Gln Gly Tyr Ala Tyr Ile Leu Thr His Pro Gly Ile Pro
305                 310                 315                 320 tgc atc ttc tac gac cat ttc ttc aac tgg ggg ttt aag gac cag atc     1008
Cys Ile Phe Tyr Asp His Phe Phe Asn Trp Gly Phe Lys Asp Gln Ile
                325                 330                 335 gcg gcg ctg gtg gcg atc agg aag cgc aac ggc atc acg gcg acg agc     1056
Ala Ala Leu Val Ala Ile Arg Lys Arg Asn Gly Ile Thr Ala Thr Ser
            340                 345                 350 gct ctg aag atc ctc atg cac gaa gga gat gcc tac gtc gcc gag ata     1104
Ala Leu Lys Ile Leu Met His Glu Gly Asp Ala Tyr Val Ala Glu Ile
        355                 360                 365 gac ggc aag gtg gtg gtg aag atc ggg tcc agg tac gac gtc ggg gcg     1152
Asp Gly Lys Val Val Val Lys Ile Gly Ser Arg Tyr Asp Val Gly Ala
    370                 375                 380 gtg atc ccg gcc ggg ttc gtg acc tcg gca cac ggc aac gac tac gcc     1200
Val Ile Pro Ala Gly Phe Val Thr Ser Ala His Gly Asn Asp Tyr Ala
385                 390                 395                 400
```

```
gtc tgg gag aag                                              1212
Val Trp Glu Lys
```

<210> SEQ ID NO 4
<211> LENGTH: 404
<212> TYPE: PRT
<213> ORGANISM: Artificial Sequence
<220> FEATURE:
<223> OTHER INFORMATION: Truncated alpha-amylase (Amy1.delta.10)

<400> SEQUENCE: 4

```
His Gln Val Leu Phe Gln Gly Phe Asn Trp Glu Ser Trp Lys Gln Ser
  1               5                  10                  15

Gly Gly Trp Tyr Asn Met Met Gly Lys Val Asp Asp Ile Ala Ala
             20                  25                  30

Ala Gly Val Thr His Val Trp Leu Pro Pro Ser His Ser Val Ser
         35                  40                  45

Asn Glu Gly Tyr Met Pro Gly Arg Leu Tyr Asp Ile Asp Ala Ser Lys
 50                  55                  60

Tyr Gly Asn Ala Ala Glu Leu Lys Ser Leu Ile Gly Ala Leu His Gly
 65                  70                  75                  80

Lys Gly Val Gln Ala Ile Ala Asp Ile Val Ile Asn His Arg Cys Ala
                 85                  90                  95

Asp Tyr Lys Asp Ser Arg Gly Ile Tyr Cys Ile Phe Glu Gly Gly Thr
                100                 105                 110

Ser Asp Gly Arg Leu Asp Trp Gly Pro His Met Ile Cys Arg Asp Asp
            115                 120                 125

Thr Lys Tyr Ser Asp Gly Thr Ala Asn Leu Asp Thr Gly Ala Asp Phe
    130                 135                 140

Ala Ala Ala Pro Asp Ile Asp His Leu Asn Asp Arg Val Gln Arg Glu
145                 150                 155                 160

Leu Lys Glu Trp Leu Leu Trp Leu Lys Ser Asp Leu Gly Phe Asp Ala
                165                 170                 175

Trp Arg Leu Asp Phe Ala Arg Gly Tyr Ser Pro Glu Met Ala Lys Val
            180                 185                 190

Tyr Ile Asp Gly Thr Ser Pro Ser Leu Ala Val Ala Glu Val Trp Asp
        195                 200                 205

Asn Met Ala Thr Gly Gly Asp Gly Lys Pro Asn Tyr Asp Gln Asp Ala
210                 215                 220

His Arg Gln Asn Leu Val Asn Trp Val Asp Lys Val Gly Gly Ala Ala
225                 230                 235                 240

Ser Ala Gly Met Val Phe Asp Phe Thr Thr Lys Gly Ile Leu Asn Ala
                245                 250                 255

Ala Val Glu Gly Glu Leu Trp Arg Leu Ile Asp Pro Gln Gly Lys Ala
            260                 265                 270

Pro Gly Val Met Gly Trp Trp Pro Ala Lys Ala Val Thr Phe Val Asp
        275                 280                 285

Asn His Asp Thr Gly Ser Thr Gln Ala Met Trp Pro Phe Pro Ser Asp
    290                 295                 300

Lys Val Met Gln Gly Tyr Ala Tyr Ile Leu Thr His Pro Gly Ile Pro
305                 310                 315                 320

Cys Ile Phe Tyr Asp His Phe Phe Asn Trp Gly Phe Lys Asp Gln Ile
                325                 330                 335

Ala Ala Leu Val Ala Ile Arg Lys Arg Asn Gly Ile Thr Ala Thr Ser
            340                 345                 350

Ala Leu Lys Ile Leu Met His Glu Gly Asp Ala Tyr Val Ala Glu Ile
```

```
                   355                 360                 365
Asp Gly Lys Val Val Lys Ile Gly Ser Arg Tyr Asp Val Gly Ala
            370                 375                 380

Val Ile Pro Ala Gly Phe Val Thr Ser Ala His Gly Asn Asp Tyr Ala
385                 390                 395                 400

Val Trp Glu Lys

<210> SEQ ID NO 5
<211> LENGTH: 1293
<212> TYPE: DNA
<213> ORGANISM: Artificial Sequence
<220> FEATURE:
<223> OTHER INFORMATION: Truncated alpha-amylase (Amy1.delta.9 with
      regulatory sequences)
<221> NAME/KEY: CDS
<222> LOCATION: (1)...(1293)

<400> SEQUENCE: 5 atg agg gtg ttg ctc gtt gcc ctc gct ctc ctg gct ctc gct gcg agc      48
Met Arg Val Leu Leu Val Ala Leu Ala Leu Leu Ala Leu Ala Ala Ser
 1               5                  10                  15 gcc acc agc cac caa gtc ctc ttt cag ggg ttc aac tgg gag tcg tgg      96
Ala Thr Ser His Gln Val Leu Phe Gln Gly Phe Asn Trp Glu Ser Trp
                20                  25                  30 aag cag agc ggc ggg tgg tac aac atg atg atg ggc aag gtc gac gac     144
Lys Gln Ser Gly Gly Trp Tyr Asn Met Met Met Gly Lys Val Asp Asp
            35                  40                  45 atc gcc gct gcc gga gtc acc cac gtc tgg ctg cca ccg ccg tcg cac     192
Ile Ala Ala Ala Gly Val Thr His Val Trp Leu Pro Pro Pro Ser His
        50                  55                  60 tcc gtc tcc aac gaa ggt tac atg cct ggt cgg ctg tac gac atc gac     240
Ser Val Ser Asn Glu Gly Tyr Met Pro Gly Arg Leu Tyr Asp Ile Asp
 65                  70                  75                  80 gcg tcc aag tac ggc aac gcg gcg gag ctc aag tcg ctc atc ggc gcg     288
Ala Ser Lys Tyr Gly Asn Ala Ala Glu Leu Lys Ser Leu Ile Gly Ala
                85                  90                  95 ctc cac ggc aag ggc gtg cag gcc atc gcc gac atc gtc atc aac cac     336
Leu His Gly Lys Gly Val Gln Ala Ile Ala Asp Ile Val Ile Asn His
            100                 105                 110 cgc tgc gcc gac tac aag gat agc cgc ggc atc tac tgc atc ttc gag     384
Arg Cys Ala Asp Tyr Lys Asp Ser Arg Gly Ile Tyr Cys Ile Phe Glu
        115                 120                 125 ggc ggc acc tcc gac ggc cgc ctc gac tgg ggc ccc cac atg atc tgt     432
Gly Gly Thr Ser Asp Gly Arg Leu Asp Trp Gly Pro His Met Ile Cys
    130                 135                 140 cgc gac gac acc aaa tac tcc gat ggc acc gca aac ctc gac acc gga     480
Arg Asp Asp Thr Lys Tyr Ser Asp Gly Thr Ala Asn Leu Asp Thr Gly
145                 150                 155                 160 gcc gac ttc gcc gcc gcg ccc gac atc gac cac ctc aac gac cgg gtc     528
Ala Asp Phe Ala Ala Ala Pro Asp Ile Asp His Leu Asn Asp Arg Val
                165                 170                 175 cag cgc gag ctc aag gag tgg ctc ctc tgg ctc aag agc gac ctc ggc     576
Gln Arg Glu Leu Lys Glu Trp Leu Leu Trp Leu Lys Ser Asp Leu Gly
            180                 185                 190 ttc gac gcg tgg cgc ctt gac ttc gcc agg ggc tac tcg ccg gag atg     624
Phe Asp Ala Trp Arg Leu Asp Phe Ala Arg Gly Tyr Ser Pro Glu Met
        195                 200                 205 gcc aag gtg tac atc gac ggc aca tcc ccg agc ctc gcc gtg gcc gag     672
Ala Lys Val Tyr Ile Asp Gly Thr Ser Pro Ser Leu Ala Val Ala Glu
    210                 215                 220 gtg tgg gac aat atg gcc acc ggc ggc gac ggc aag ccc aac tac gac     720
Val Trp Asp Asn Met Ala Thr Gly Gly Asp Gly Lys Pro Asn Tyr Asp
```

```
Val Trp Asp Asn Met Ala Thr Gly Gly Asp Gly Lys Pro Asn Tyr Asp
225                 230                 235                 240 cag gac gcg cac cgg cag aat ctg gtg aac tgg gtg gac aag gtg ggc    768
Gln Asp Ala His Arg Gln Asn Leu Val Asn Trp Val Asp Lys Val Gly
                245                 250                 255 ggc gcg gcc tcg gca ggc atg gtg ttc gac ttc acg acc aaa ggg ata    816
Gly Ala Ala Ser Ala Gly Met Val Phe Asp Phe Thr Thr Lys Gly Ile
                260                 265                 270 ctg aac gct gcc gtg gag ggc gag ctg tgg agg ctg atc gac ccg cag    864
Leu Asn Ala Ala Val Glu Gly Glu Leu Trp Arg Leu Ile Asp Pro Gln
                275                 280                 285 ggg aag gcc ccc ggc gtg atg gga tgg tgg ccg gcc aag gcc gtc acc    912
Gly Lys Ala Pro Gly Val Met Gly Trp Trp Pro Ala Lys Ala Val Thr
            290                 295                 300 ttc gtc gac aac cac gat aca ggc tcc acg cag gcc atg tgg cca ttc    960
Phe Val Asp Asn His Asp Thr Gly Ser Thr Gln Ala Met Trp Pro Phe
305                 310                 315                 320 ccc tcc gac aag gtc atg cag ggc tac gcg tac atc ctc acc cac ccc   1008
Pro Ser Asp Lys Val Met Gln Gly Tyr Ala Tyr Ile Leu Thr His Pro
                325                 330                 335 ggc atc cca tgc atc ttc tac gac cat ttc ttc aac tgg ggg ttt aag   1056
Gly Ile Pro Cys Ile Phe Tyr Asp His Phe Phe Asn Trp Gly Phe Lys
                340                 345                 350 gac cag atc gcg gcg ctg gtg gcg atc agg aag cgc aac ggc atc acg   1104
Asp Gln Ile Ala Ala Leu Val Ala Ile Arg Lys Arg Asn Gly Ile Thr
                355                 360                 365 gcg acg agc gct ctg aag atc ctc atg cac gaa gga gat gcc tac gtc   1152
Ala Thr Ser Ala Leu Lys Ile Leu Met His Glu Gly Asp Ala Tyr Val
370                 375                 380 gcc gag ata gac ggc aag gtg gtg gtg aag atc ggg tcc agg tac gac   1200
Ala Glu Ile Asp Gly Lys Val Val Val Lys Ile Gly Ser Arg Tyr Asp
385                 390                 395                 400 gtc ggg gcg gtg atc ccg gcc ggg ttc gtg acc tcg gca cac ggc aac   1248
Val Gly Ala Val Ile Pro Ala Gly Phe Val Thr Ser Ala His Gly Asn
                405                 410                 415 gac tac gcc gtc tgg gag aag aac tcc gag aag gac gag ctg tag        1293
Asp Tyr Ala Val Trp Glu Lys Asn Ser Glu Lys Asp Glu Leu *
                420                 425                 430

<210> SEQ ID NO 6
<211> LENGTH: 430
<212> TYPE: PRT
<213> ORGANISM: Artificial Sequence
<220> FEATURE:
<223> OTHER INFORMATION: Truncated alpha-amylase (Amy1.delta.9 with
      regulatory sequences)

<400> SEQUENCE: 6

Met Arg Val Leu Leu Val Ala Leu Ala Leu Leu Ala Leu Ala Ala Ser
1               5                   10                  15

Ala Thr Ser His Gln Val Leu Phe Gln Gly Phe Asn Trp Glu Ser Trp
                20                  25                  30

Lys Gln Ser Gly Gly Trp Tyr Asn Met Met Gly Lys Val Asp Asp
            35                  40                  45

Ile Ala Ala Ala Gly Val Thr His Val Trp Leu Pro Pro Pro Ser His
        50                  55                  60

Ser Val Ser Asn Glu Gly Tyr Met Pro Gly Arg Leu Tyr Asp Ile Asp
65                  70                  75                  80

Ala Ser Lys Tyr Gly Asn Ala Ala Glu Leu Lys Ser Leu Ile Gly Ala
                85                  90                  95
```

```
Leu His Gly Lys Gly Val Gln Ala Ile Ala Asp Ile Val Ile Asn His
            100                 105                 110
Arg Cys Ala Asp Tyr Lys Asp Ser Arg Gly Ile Tyr Cys Ile Phe Glu
        115                 120                 125
Gly Gly Thr Ser Asp Gly Arg Leu Asp Trp Gly Pro His Met Ile Cys
130                 135                 140
Arg Asp Asp Thr Lys Tyr Ser Asp Gly Thr Ala Asn Leu Asp Thr Gly
145                 150                 155                 160
Ala Asp Phe Ala Ala Ala Pro Asp Ile Asp His Leu Asn Asp Arg Val
                165                 170                 175
Gln Arg Glu Leu Lys Glu Trp Leu Leu Trp Leu Lys Ser Asp Leu Gly
            180                 185                 190
Phe Asp Ala Trp Arg Leu Asp Phe Ala Arg Gly Tyr Ser Pro Glu Met
        195                 200                 205
Ala Lys Val Tyr Ile Asp Gly Thr Ser Pro Ser Leu Ala Val Ala Glu
210                 215                 220
Val Trp Asp Asn Met Ala Thr Gly Gly Asp Gly Lys Pro Asn Tyr Asp
225                 230                 235                 240
Gln Asp Ala His Arg Gln Asn Leu Val Asn Trp Val Asp Lys Val Gly
                245                 250                 255
Gly Ala Ala Ser Ala Gly Met Val Phe Asp Phe Thr Thr Lys Gly Ile
            260                 265                 270
Leu Asn Ala Ala Val Glu Gly Glu Leu Trp Arg Leu Ile Asp Pro Gln
        275                 280                 285
Gly Lys Ala Pro Gly Val Met Gly Trp Trp Pro Ala Lys Ala Val Thr
290                 295                 300
Phe Val Asp Asn His Asp Thr Gly Ser Thr Gln Ala Met Trp Pro Phe
305                 310                 315                 320
Pro Ser Asp Lys Val Met Gln Gly Tyr Ala Tyr Ile Leu Thr His Pro
                325                 330                 335
Gly Ile Pro Cys Ile Phe Tyr Asp His Phe Phe Asn Trp Gly Phe Lys
            340                 345                 350
Asp Gln Ile Ala Ala Leu Val Ala Ile Arg Lys Arg Asn Gly Ile Thr
        355                 360                 365
Ala Thr Ser Ala Leu Lys Ile Leu Met His Glu Gly Asp Ala Tyr Val
370                 375                 380
Ala Glu Ile Asp Gly Lys Val Val Lys Ile Gly Ser Arg Tyr Asp
385                 390                 395                 400
Val Gly Ala Val Ile Pro Ala Gly Phe Val Thr Ser Ala His Gly Asn
                405                 410                 415
Asp Tyr Ala Val Trp Glu Lys Asn Ser Glu Lys Asp Glu Leu
            420                 425                 430

<210> SEQ ID NO 7
<211> LENGTH: 1290
<212> TYPE: DNA
<213> ORGANISM: Artificial Sequence
<220> FEATURE:
<223> OTHER INFORMATION: Truncated alpha-amylase (Amy1.delta.10 with
      regulatory sequences)
<221> NAME/KEY: CDS
<222> LOCATION: (1)...(1290)

<400> SEQUENCE: 7 atg agg gtg ttg ctc gtt gcc ctc gct ctc ctg gct ctc gct gcg agc      48
Met Arg Val Leu Leu Val Ala Leu Ala Leu Leu Ala Leu Ala Ala Ser
 1               5                   10                  15
```

```
gcc acc agc cac caa gtc ctc ttt cag ggg ttc aac tgg gag tcg tgg        96
Ala Thr Ser His Gln Val Leu Phe Gln Gly Phe Asn Trp Glu Ser Trp
             20                  25                  30 aag cag agc ggc ggg tgg tac aac atg atg atg ggc aag gtc gac gac       144
Lys Gln Ser Gly Gly Trp Tyr Asn Met Met Met Gly Lys Val Asp Asp
         35                  40                  45 atc gcc gct gcc gga gtc acc cac gtc tgg ctg cca ccg ccg tcg cac       192
Ile Ala Ala Ala Gly Val Thr His Val Trp Leu Pro Pro Pro Ser His
     50                  55                  60 tcc gtc tcc aac gaa ggt tac atg cct ggt cgg ctg tac gac atc gac       240
Ser Val Ser Asn Glu Gly Tyr Met Pro Gly Arg Leu Tyr Asp Ile Asp
 65                  70                  75                  80 gcg tcc aag tac ggc aac gcg gcg gag ctc aag tcg ctc atc ggc gcg       288
Ala Ser Lys Tyr Gly Asn Ala Ala Glu Leu Lys Ser Leu Ile Gly Ala
                 85                  90                  95 ctc cac ggc aag ggc gtg cag gcc atc gcc gac atc gtc atc aac cac       336
Leu His Gly Lys Gly Val Gln Ala Ile Ala Asp Ile Val Ile Asn His
            100                 105                 110 cgc tgc gcc gac tac aag gat agc cgc ggc atc tac tgc atc ttc gag       384
Arg Cys Ala Asp Tyr Lys Asp Ser Arg Gly Ile Tyr Cys Ile Phe Glu
        115                 120                 125 ggc ggc acc tcc gac ggc cgc ctc gac tgg ggc ccc cac atg atc tgt       432
Gly Gly Thr Ser Asp Gly Arg Leu Asp Trp Gly Pro His Met Ile Cys
    130                 135                 140 cgc gac gac acc aaa tac tcc gat ggc acc gca aac ctc gac acc gga       480
Arg Asp Asp Thr Lys Tyr Ser Asp Gly Thr Ala Asn Leu Asp Thr Gly
145                 150                 155                 160 gcc gac ttc gcc gcc gcg ccc gac atc gac cac ctc aac gac cgg gtc       528
Ala Asp Phe Ala Ala Ala Pro Asp Ile Asp His Leu Asn Asp Arg Val
                165                 170                 175 cag cgc gag ctc aag gag tgg ctc ctc tgg ctc aag agc gac ctc ggc       576
Gln Arg Glu Leu Lys Glu Trp Leu Leu Trp Leu Lys Ser Asp Leu Gly
            180                 185                 190 ttc gac gcg tgg cgc ctt gac ttc gcc agg ggc tac tcg ccg gag atg       624
Phe Asp Ala Trp Arg Leu Asp Phe Ala Arg Gly Tyr Ser Pro Glu Met
        195                 200                 205 gcc aag gtg tac atc gac ggc aca tcc ccg agc ctc gcc gtg gcc gag       672
Ala Lys Val Tyr Ile Asp Gly Thr Ser Pro Ser Leu Ala Val Ala Glu
    210                 215                 220 gtg tgg gac aat atg gcc acc ggc ggc gac ggc aag ccc aac tac gac       720
Val Trp Asp Asn Met Ala Thr Gly Gly Asp Gly Lys Pro Asn Tyr Asp
225                 230                 235                 240 cag gac gcg cac cgg cag aat ctg gtg aac tgg gtg gac aag gtg ggc       768
Gln Asp Ala His Arg Gln Asn Leu Val Asn Trp Val Asp Lys Val Gly
                245                 250                 255 ggc gcg gcc tcg gca ggc atg gtg ttc gac ttc acg acc aaa ggg ata       816
Gly Ala Ala Ser Ala Gly Met Val Phe Asp Phe Thr Thr Lys Gly Ile
            260                 265                 270 ctg aac gct gcc gtg gag ggc gag ctg tgg agg ctg atc gac ccg cag       864
Leu Asn Ala Ala Val Glu Gly Glu Leu Trp Arg Leu Ile Asp Pro Gln
        275                 280                 285 ggg aag gcc ccc ggc gtg atg gga tgg tgg ccg gcc aag gcc gtc acc       912
Gly Lys Ala Pro Gly Val Met Gly Trp Trp Pro Ala Lys Ala Val Thr
    290                 295                 300 ttc gtc gac aac cac gat aca ggc tcc acg cag gcc atg tgg cca ttc       960
Phe Val Asp Asn His Asp Thr Gly Ser Thr Gln Ala Met Trp Pro Phe
305                 310                 315                 320 ccc tcc gac aag gtc atg cag ggc tac gcg tac atc ctc acc cac ccc      1008
Pro Ser Asp Lys Val Met Gln Gly Tyr Ala Tyr Ile Leu Thr His Pro
                325                 330                 335
```

```
ggc atc cca tgc atc ttc tac gac cat ttc ttc aac tgg ggg ttt aag      1056
Gly Ile Pro Cys Ile Phe Tyr Asp His Phe Phe Asn Trp Gly Phe Lys
            340                 345                 350 gac cag atc gcg gcg ctg gtg gcg atc agg aag cgc aac ggc atc acg      1104
Asp Gln Ile Ala Ala Leu Val Ala Ile Arg Lys Arg Asn Gly Ile Thr
        355                 360                 365 gcg acg agc gct ctg aag atc ctc atg cac gaa gga gat gcc tac gtc      1152
Ala Thr Ser Ala Leu Lys Ile Leu Met His Glu Gly Asp Ala Tyr Val
    370                 375                 380 gcc gag ata gac ggc aag gtg gtg gtg aag atc ggg tcc agg tac gac      1200
Ala Glu Ile Asp Gly Lys Val Val Val Lys Ile Gly Ser Arg Tyr Asp
385                 390                 395                 400 gtc ggg gcg gtg atc ccg gcc ggg ttc gtg acc tcg gca cac ggc aac      1248
Val Gly Ala Val Ile Pro Ala Gly Phe Val Thr Ser Ala His Gly Asn
                405                 410                 415 gac tac gcc gtc tgg gag aag tcc gag aag gac gag ctg tag              1290
Asp Tyr Ala Val Trp Glu Lys Ser Glu Lys Asp Glu Leu  *
                420                 425
```

<210> SEQ ID NO 8
<211> LENGTH: 429
<212> TYPE: PRT
<213> ORGANISM: Artificial Sequence
<220> FEATURE:
<223> OTHER INFORMATION: Truncated alpha-amylase (Amy1.delta.10 with regulatory sequences)

<400> SEQUENCE: 8

```
Met Arg Val Leu Leu Val Ala Leu Ala Leu Leu Ala Leu Ala Ala Ser
  1               5                  10                  15

Ala Thr Ser His Gln Val Leu Phe Gln Gly Phe Asn Trp Glu Ser Trp
                 20                  25                  30

Lys Gln Ser Gly Gly Trp Tyr Asn Met Met Met Gly Lys Val Asp Asp
             35                  40                  45

Ile Ala Ala Gly Val Thr His Val Trp Leu Pro Pro Ser His
         50                  55                  60

Ser Val Ser Asn Glu Gly Tyr Met Pro Gly Arg Leu Tyr Asp Ile Asp
 65                  70                  75                  80

Ala Ser Lys Tyr Gly Asn Ala Ala Glu Leu Lys Ser Leu Ile Gly Ala
                 85                  90                  95

Leu His Gly Lys Gly Val Gln Ala Ile Ala Asp Ile Val Ile Asn His
            100                 105                 110

Arg Cys Ala Asp Tyr Lys Asp Ser Arg Gly Ile Tyr Cys Ile Phe Glu
        115                 120                 125

Gly Gly Thr Ser Asp Gly Arg Leu Asp Trp Gly Pro His Met Ile Cys
    130                 135                 140

Arg Asp Asp Thr Lys Tyr Ser Asp Gly Thr Ala Asn Leu Asp Thr Gly
145                 150                 155                 160

Ala Asp Phe Ala Ala Ala Pro Asp Ile Asp His Leu Asn Asp Arg Val
                165                 170                 175

Gln Arg Glu Leu Lys Glu Trp Leu Leu Trp Leu Lys Ser Asp Leu Gly
            180                 185                 190

Phe Asp Ala Trp Arg Leu Asp Phe Ala Arg Gly Tyr Ser Pro Glu Met
        195                 200                 205

Ala Lys Val Tyr Ile Asp Gly Thr Ser Pro Ser Leu Ala Val Ala Glu
    210                 215                 220

Val Trp Asp Asn Met Ala Thr Gly Gly Asp Gly Lys Pro Asn Tyr Asp
225                 230                 235                 240
```

```
Gln Asp Ala His Arg Gln Asn Leu Val Asn Trp Val Asp Lys Val Gly
                245                 250                 255

Gly Ala Ala Ser Ala Gly Met Val Phe Asp Phe Thr Thr Lys Gly Ile
            260                 265                 270

Leu Asn Ala Ala Val Glu Gly Glu Leu Trp Arg Leu Ile Asp Pro Gln
        275                 280                 285

Gly Lys Ala Pro Gly Val Met Gly Trp Trp Pro Ala Lys Ala Val Thr
    290                 295                 300

Phe Val Asp Asn His Asp Thr Gly Ser Thr Gln Ala Met Trp Pro Phe
305                 310                 315                 320

Pro Ser Asp Lys Val Met Gln Gly Tyr Ala Tyr Ile Leu Thr His Pro
                325                 330                 335

Gly Ile Pro Cys Ile Phe Tyr Asp His Phe Phe Asn Trp Gly Phe Lys
            340                 345                 350

Asp Gln Ile Ala Ala Leu Val Ala Ile Arg Lys Arg Asn Gly Ile Thr
        355                 360                 365

Ala Thr Ser Ala Leu Lys Ile Leu Met His Glu Gly Asp Ala Tyr Val
    370                 375                 380

Ala Glu Ile Asp Gly Lys Val Val Val Lys Ile Gly Ser Arg Tyr Asp
385                 390                 395                 400

Val Gly Ala Val Ile Pro Ala Gly Phe Val Thr Ser Ala His Gly Asn
                405                 410                 415

Asp Tyr Ala Val Trp Glu Lys Ser Glu Lys Asp Glu Leu
            420                 425

<210> SEQ ID NO 9
<211> LENGTH: 1242
<212> TYPE: DNA
<213> ORGANISM: Hordeum vulgare
<220> FEATURE:
<221> NAME/KEY: CDS
<222> LOCATION: (1)...(1242)

<400> SEQUENCE: 9 cac caa gtc ctc ttt cag ggg ttc aac tgg gag tcg tgg aag cag agc      48
His Gln Val Leu Phe Gln Gly Phe Asn Trp Glu Ser Trp Lys Gln Ser
  1               5                  10                  15 ggc ggg tgg tac aac atg atg atg ggc aag gtc gac gac atc gcc gct      96
Gly Gly Trp Tyr Asn Met Met Met Gly Lys Val Asp Asp Ile Ala Ala
             20                  25                  30 gcc gga gtc acc cac gtc tgg ctg cca ccg ccg tcg cac tcc gtc tcc     144
Ala Gly Val Thr His Val Trp Leu Pro Pro Pro Ser His Ser Val Ser
         35                  40                  45 aac gaa ggt tac atg cct ggt cgg ctg tac gac atc gac gcg tcc aag     192
Asn Glu Gly Tyr Met Pro Gly Arg Leu Tyr Asp Ile Asp Ala Ser Lys
     50                  55                  60 tac ggc aac gcg gcg gag ctc aag tcg ctc atc ggc gcg ctc cac ggc     240
Tyr Gly Asn Ala Ala Glu Leu Lys Ser Leu Ile Gly Ala Leu His Gly
 65                  70                  75                  80 aag ggc gtg cag gcc atc gcc gac atc gtc atc aac cac cgc tgc gcc     288
Lys Gly Val Gln Ala Ile Ala Asp Ile Val Ile Asn His Arg Cys Ala
                 85                  90                  95 gac tac aag gat agc cgc ggc atc tac tgc atc ttc gag ggc ggc acc     336
Asp Tyr Lys Asp Ser Arg Gly Ile Tyr Cys Ile Phe Glu Gly Gly Thr
            100                 105                 110 tcc gac ggc cgc ctc gac tgg ggc ccc cac atg atc tgt cgc gac gac     384
Ser Asp Gly Arg Leu Asp Trp Gly Pro His Met Ile Cys Arg Asp Asp
        115                 120                 125 acc aaa tac tcc gat ggc acc gca aac ctc gac acc gga gcc gac ttc     432
```

```
                Thr Lys Tyr Ser Asp Gly Thr Ala Asn Leu Asp Thr Gly Ala Asp Phe
                                130                 135                 140 gcc gcc gcg ccc gac atc gac cac ctc aac gac cgg gtc cag cgc gag          480
Ala Ala Ala Pro Asp Ile Asp His Leu Asn Asp Arg Val Gln Arg Glu
145                 150                 155                 160 ctc aag gag tgg ctc ctc tgg ctc aag agc gac ctc ggc ttc gac gcg          528
Leu Lys Glu Trp Leu Leu Trp Leu Lys Ser Asp Leu Gly Phe Asp Ala
                165                 170                 175 tgg cgc ctt gac ttc gcc agg ggc tac tcg ccg gag atg gcc aag gtg          576
Trp Arg Leu Asp Phe Ala Arg Gly Tyr Ser Pro Glu Met Ala Lys Val
            180                 185                 190 tac atc gac ggc aca tcc ccg agc ctc gcc gtg gcc gag gtg tgg gac          624
Tyr Ile Asp Gly Thr Ser Pro Ser Leu Ala Val Ala Glu Val Trp Asp
        195                 200                 205 aat atg gcc acc ggc ggc gac ggc aag ccc aac tac gac cag gac gcg          672
Asn Met Ala Thr Gly Gly Asp Gly Lys Pro Asn Tyr Asp Gln Asp Ala
210                 215                 220 cac cgg cag aat ctg gtg aac tgg gtg gac aag gtg ggc ggc gcg gcc          720
His Arg Gln Asn Leu Val Asn Trp Val Asp Lys Val Gly Gly Ala Ala
225                 230                 235                 240 tcg gca ggc atg gtg ttc gac ttc acg acc aaa ggg ata ctg aac gct          768
Ser Ala Gly Met Val Phe Asp Phe Thr Thr Lys Gly Ile Leu Asn Ala
                245                 250                 255 gcc gtg gag ggc gag ctg tgg agg ctg atc gac ccg cag ggg aag gcc          816
Ala Val Glu Gly Glu Leu Trp Arg Leu Ile Asp Pro Gln Gly Lys Ala
            260                 265                 270 ccc ggc gtg atg gga tgg tgg ccg gcc aag gcc gtc acc ttc gtc gac          864
Pro Gly Val Met Gly Trp Trp Pro Ala Lys Ala Val Thr Phe Val Asp
        275                 280                 285 aac cac gat aca ggc tcc acg cag gcc atg tgg cca ttc ccc tcc gac          912
Asn His Asp Thr Gly Ser Thr Gln Ala Met Trp Pro Phe Pro Ser Asp
290                 295                 300 aag gtc atg cag ggc tac gcg tac atc ctc acc cac ccc ggc atc cca          960
Lys Val Met Gln Gly Tyr Ala Tyr Ile Leu Thr His Pro Gly Ile Pro
305                 310                 315                 320 tgc atc ttc tac gac cat ttc ttc aac tgg ggg ttt aag gac cag atc         1008
Cys Ile Phe Tyr Asp His Phe Phe Asn Trp Gly Phe Lys Asp Gln Ile
                325                 330                 335 gcg gcg ctg gtg gcg atc agg aag cgc aac ggc atc acg gcg acg agc         1056
Ala Ala Leu Val Ala Ile Arg Lys Arg Asn Gly Ile Thr Ala Thr Ser
            340                 345                 350 gct ctg aag atc ctc atg cac gaa gga gat gcc tac gtc gcc gag ata         1104
Ala Leu Lys Ile Leu Met His Glu Gly Asp Ala Tyr Val Ala Glu Ile
        355                 360                 365 gac ggc aag gtg gtg gtg aag atc ggg tcc agg tac gac gtc ggg gcg         1152
Asp Gly Lys Val Val Val Lys Ile Gly Ser Arg Tyr Asp Val Gly Ala
370                 375                 380 gtg atc ccg gcc ggg ttc gtg acc tcg gca cac ggc aac gac tac gcc         1200
Val Ile Pro Ala Gly Phe Val Thr Ser Ala His Gly Asn Asp Tyr Ala
385                 390                 395                 400 gtc tgg gag aag aac ggt gcc gcg gca aca cta caa cgg agc                 1242
Val Trp Glu Lys Asn Gly Ala Ala Ala Thr Leu Gln Arg Ser
                405                 410

<210> SEQ ID NO 10
<211> LENGTH: 414
<212> TYPE: PRT
<213> ORGANISM: Hordeum vulgare

<400> SEQUENCE: 10

His Gln Val Leu Phe Gln Gly Phe Asn Trp Glu Ser Trp Lys Gln Ser
```

```
                1               5                   10                  15
        Gly Gly Trp Tyr Asn Met Met Gly Lys Val Asp Asp Ile Ala Ala
                        20                  25                  30

Ala Gly Val Thr His Val Trp Leu Pro Pro Ser His Ser Val Ser
                        35                  40                  45

Asn Glu Gly Tyr Met Pro Gly Arg Leu Tyr Asp Ile Asp Ala Ser Lys
                    50                  55                  60

Tyr Gly Asn Ala Ala Glu Leu Lys Ser Leu Ile Gly Ala Leu His Gly
        65                  70                  75                  80

Lys Gly Val Gln Ala Ile Ala Asp Ile Val Ile Asn His Arg Cys Ala
                            85                  90                  95

Asp Tyr Lys Asp Ser Arg Gly Ile Tyr Cys Ile Phe Glu Gly Gly Thr
                        100                 105                 110

Ser Asp Gly Arg Leu Asp Trp Gly Pro His Met Ile Cys Arg Asp Asp
                    115                 120                 125

Thr Lys Tyr Ser Asp Gly Thr Ala Asn Leu Asp Thr Gly Ala Asp Phe
                    130                 135                 140

Ala Ala Ala Pro Asp Ile Asp His Leu Asn Asp Arg Val Gln Arg Glu
        145                 150                 155                 160

Leu Lys Glu Trp Leu Leu Trp Leu Lys Ser Asp Leu Gly Phe Asp Ala
                        165                 170                 175

Trp Arg Leu Asp Phe Ala Arg Gly Tyr Ser Pro Glu Met Ala Lys Val
                        180                 185                 190

Tyr Ile Asp Gly Thr Ser Pro Ser Leu Ala Val Ala Glu Val Trp Asp
                        195                 200                 205

Asn Met Ala Thr Gly Gly Asp Gly Lys Pro Asn Tyr Asp Gln Asp Ala
                        210                 215                 220

His Arg Gln Asn Leu Val Asn Trp Val Asp Lys Val Gly Gly Ala Ala
        225                 230                 235                 240

Ser Ala Gly Met Val Phe Asp Phe Thr Thr Lys Gly Ile Leu Asn Ala
                        245                 250                 255

Ala Val Glu Gly Glu Leu Trp Arg Leu Ile Asp Pro Gln Gly Lys Ala
                        260                 265                 270

Pro Gly Val Met Gly Trp Trp Pro Ala Lys Ala Val Thr Phe Val Asp
                        275                 280                 285

Asn His Asp Thr Gly Ser Thr Gln Ala Met Trp Pro Phe Pro Ser Asp
                        290                 295                 300

Lys Val Met Gln Gly Tyr Ala Tyr Ile Leu Thr His Pro Gly Ile Pro
        305                 310                 315                 320

Cys Ile Phe Tyr Asp His Phe Phe Asn Trp Gly Phe Lys Asp Gln Ile
                        325                 330                 335

Ala Ala Leu Val Ala Ile Arg Lys Arg Asn Gly Ile Thr Ala Thr Ser
                        340                 345                 350

Ala Leu Lys Ile Leu Met His Glu Gly Asp Ala Tyr Val Ala Glu Ile
                        355                 360                 365

Asp Gly Lys Val Val Lys Ile Gly Ser Arg Tyr Asp Val Gly Ala
                        370                 375                 380

Val Ile Pro Ala Gly Phe Val Thr Ser Ala His Gly Asn Asp Tyr Ala
        385                 390                 395                 400

Val Trp Glu Lys Asn Gly Ala Ala Ala Thr Leu Gln Arg Ser
                        405                 410

<210> SEQ ID NO 11
<211> LENGTH: 1326
```

```
<212> TYPE: DNA
<213> ORGANISM: Artificial Sequence
<220> FEATURE:
<223> OTHER INFORMATION: Barley alpha-amylase with regulatory sequences
<221> NAME/KEY: CDS
<222> LOCATION: (1)...(1326)

<400> SEQUENCE: 11 atg agg gtg ttg ctc gtt gcc ctc gct ctc ctg gct ctc gct gcg agc      48
Met Arg Val Leu Leu Val Ala Leu Ala Leu Leu Ala Leu Ala Ala Ser
 1               5                  10                  15 gcc acc tcc atg gca cac caa gtc ctc ttt cag ggg ttc aac tgg gag      96
Ala Thr Ser Met Ala His Gln Val Leu Phe Gln Gly Phe Asn Trp Glu
             20                  25                  30 tcg tgg aag cag agc ggc ggg tgg tac aac atg atg atg ggc aag gtc     144
Ser Trp Lys Gln Ser Gly Gly Trp Tyr Asn Met Met Met Gly Lys Val
         35                  40                  45 gac gac atc gcc gct gcc gga gtc acc cac gtc tgg ctg cca ccg ccg     192
Asp Asp Ile Ala Ala Ala Gly Val Thr His Val Trp Leu Pro Pro Pro
 50                  55                  60 tcg cac tcc gtc tcc aac gaa ggt tac atg cct ggt cgg ctg tac gac     240
Ser His Ser Val Ser Asn Glu Gly Tyr Met Pro Gly Arg Leu Tyr Asp
 65                  70                  75                  80 atc gac gcg tcc aag tac ggc aac gcg gcg gag ctc aag tcg ctc atc     288
Ile Asp Ala Ser Lys Tyr Gly Asn Ala Ala Glu Leu Lys Ser Leu Ile
                 85                  90                  95 ggc gcg ctc cac ggc aag ggc gtg cag gcc atc gcc gac atc gtc atc     336
Gly Ala Leu His Gly Lys Gly Val Gln Ala Ile Ala Asp Ile Val Ile
            100                 105                 110 aac cac cgc tgc gcc gac tac aag gat agc cgc ggc atc tac tgc atc     384
Asn His Arg Cys Ala Asp Tyr Lys Asp Ser Arg Gly Ile Tyr Cys Ile
        115                 120                 125 ttc gag ggc ggc acc tcc gac ggc cgc ctc gac tgg ggc ccc cac atg     432
Phe Glu Gly Gly Thr Ser Asp Gly Arg Leu Asp Trp Gly Pro His Met
130                 135                 140 atc tgt cgc gac gac acc aaa tac tcc gat ggc acc gca aac ctc gac     480
Ile Cys Arg Asp Asp Thr Lys Tyr Ser Asp Gly Thr Ala Asn Leu Asp
145                 150                 155                 160 acc gga gcc gac ttc gcc gcc gcg ccc gac atc gac cac ctc aac gac     528
Thr Gly Ala Asp Phe Ala Ala Ala Pro Asp Ile Asp His Leu Asn Asp
                165                 170                 175 cgg gtc cag cgc gag ctc aag gag tgg ctc ctc tgg ctc aag agc gac     576
Arg Val Gln Arg Glu Leu Lys Glu Trp Leu Leu Trp Leu Lys Ser Asp
            180                 185                 190 ctc ggc ttc gac gcg tgg cgc ctt gac ttc gcc agg ggc tac tcg ccg     624
Leu Gly Phe Asp Ala Trp Arg Leu Asp Phe Ala Arg Gly Tyr Ser Pro
        195                 200                 205 gag atg gcc aag gtg tac atc gac ggc aca tcc ccg agc ctc gcc gtg     672
Glu Met Ala Lys Val Tyr Ile Asp Gly Thr Ser Pro Ser Leu Ala Val
210                 215                 220 gcc gag gtg tgg gac aat atg gcc acc ggc ggc gac ggc aag ccc aac     720
Ala Glu Val Trp Asp Asn Met Ala Thr Gly Gly Asp Gly Lys Pro Asn
225                 230                 235                 240 tac gac cag gac gcg cac cgg cag aat ctg gtg aac tgg gtg gac aag     768
Tyr Asp Gln Asp Ala His Arg Gln Asn Leu Val Asn Trp Val Asp Lys
                245                 250                 255 gtg ggc ggc gcg gcc tcg gca ggc atg gtg ttc gac ttc acg acc aaa     816
Val Gly Gly Ala Ala Ser Ala Gly Met Val Phe Asp Phe Thr Thr Lys
            260                 265                 270 ggg ata ctg aac gct gcc gtg gag ggc gag ctg tgg agg ctg atc gac     864
Gly Ile Leu Asn Ala Ala Val Glu Gly Glu Leu Trp Arg Leu Ile Asp
        275                 280                 285
```

```
ccg cag ggg aag gcc ccc ggc gtg atg gga tgg tgg ccg gcc aag gcc      912
Pro Gln Gly Lys Ala Pro Gly Val Met Gly Trp Trp Pro Ala Lys Ala
    290                 295                 300 gtc acc ttc gtc gac aac cac gat aca ggc tcc acg cag gcc atg tgg      960
Val Thr Phe Val Asp Asn His Asp Thr Gly Ser Thr Gln Ala Met Trp
305                 310                 315                 320 cca ttc ccc tcc gac aag gtc atg cag ggc tac gcg tac atc ctc acc     1008
Pro Phe Pro Ser Asp Lys Val Met Gln Gly Tyr Ala Tyr Ile Leu Thr
                325                 330                 335 cac ccc ggc atc cca tgc atc ttc tac gac cat ttc ttc aac tgg ggg     1056
His Pro Gly Ile Pro Cys Ile Phe Tyr Asp His Phe Phe Asn Trp Gly
            340                 345                 350 ttt aag gac cag atc gcg gcg ctg gtg gcg atc agg aag cgc aac ggc     1104
Phe Lys Asp Gln Ile Ala Ala Leu Val Ala Ile Arg Lys Arg Asn Gly
        355                 360                 365 atc acg gcg acg agc gct ctg aag atc ctc atg cac gaa gga gat gcc     1152
Ile Thr Ala Thr Ser Ala Leu Lys Ile Leu Met His Glu Gly Asp Ala
    370                 375                 380 tac gtc gcc gag ata gac ggc aag gtg gtg gtg aag atc ggg tcc agg     1200
Tyr Val Ala Glu Ile Asp Gly Lys Val Val Val Lys Ile Gly Ser Arg
385                 390                 395                 400 tac gac gtc ggg gcg gtg atc ccg gcc ggg ttc gtg acc tcg gca cac     1248
Tyr Asp Val Gly Ala Val Ile Pro Ala Gly Phe Val Thr Ser Ala His
                405                 410                 415 ggc aac gac tac gcc gtc tgg gag aag aac ggt gcc gcg gca aca cta     1296
Gly Asn Asp Tyr Ala Val Trp Glu Lys Asn Gly Ala Ala Ala Thr Leu
            420                 425                 430 caa cgg agc tcc gag aag gac gag ctg tag                             1326
Gln Arg Ser Ser Glu Lys Asp Glu Leu *
        435                 440

<210> SEQ ID NO 12
<211> LENGTH: 441
<212> TYPE: PRT
<213> ORGANISM: Artificial Sequence
<220> FEATURE:
<223> OTHER INFORMATION: Barley alpha-amylase with regulatory sequences

<400> SEQUENCE: 12

Met Arg Val Leu Leu Val Ala Leu Ala Leu Ala Leu Ala Ala Ser
1               5                   10                  15

Ala Thr Ser Met Ala His Gln Val Leu Phe Gln Gly Phe Asn Trp Glu
            20                  25                  30

Ser Trp Lys Gln Ser Gly Gly Trp Tyr Asn Met Met Gly Lys Val
        35                  40                  45

Asp Asp Ile Ala Ala Ala Gly Val Thr His Val Trp Leu Pro Pro Pro
    50                  55                  60

Ser His Ser Val Ser Asn Glu Gly Tyr Met Pro Gly Arg Leu Tyr Asp
65                  70                  75                  80

Ile Asp Ala Ser Lys Tyr Gly Asn Ala Ala Glu Leu Lys Ser Leu Ile
                85                  90                  95

Gly Ala Leu His Gly Lys Gly Val Gln Ala Ile Ala Asp Ile Val Ile
            100                 105                 110

Asn His Arg Cys Ala Asp Tyr Lys Asp Ser Arg Gly Ile Tyr Cys Ile
        115                 120                 125

Phe Glu Gly Gly Thr Ser Asp Gly Arg Leu Asp Trp Gly Pro His Met
    130                 135                 140

Ile Cys Arg Asp Asp Thr Lys Tyr Ser Asp Gly Thr Ala Asn Leu Asp
145                 150                 155                 160
```

```
Thr Gly Ala Asp Phe Ala Ala Ala Pro Asp Ile Asp His Leu Asn Asp
            165                 170                 175

Arg Val Gln Arg Glu Leu Lys Glu Trp Leu Leu Trp Leu Lys Ser Asp
            180                 185                 190

Leu Gly Phe Asp Ala Trp Arg Leu Asp Phe Ala Arg Gly Tyr Ser Pro
            195                 200                 205

Glu Met Ala Lys Val Tyr Ile Asp Gly Thr Ser Pro Ser Leu Ala Val
            210                 215                 220

Ala Glu Val Trp Asp Asn Met Ala Thr Gly Gly Asp Gly Lys Pro Asn
225                 230                 235                 240

Tyr Asp Gln Asp Ala His Arg Gln Asn Leu Val Asn Trp Val Asp Lys
            245                 250                 255

Val Gly Gly Ala Ala Ser Ala Gly Met Val Phe Asp Phe Thr Thr Lys
            260                 265                 270

Gly Ile Leu Asn Ala Ala Val Glu Gly Glu Leu Trp Arg Leu Ile Asp
            275                 280                 285

Pro Gln Gly Lys Ala Pro Gly Val Met Gly Trp Trp Pro Ala Lys Ala
            290                 295                 300

Val Thr Phe Val Asp Asn His Asp Thr Gly Ser Thr Gln Ala Met Trp
305                 310                 315                 320

Pro Phe Pro Ser Asp Lys Val Met Gln Gly Tyr Ala Tyr Ile Leu Thr
            325                 330                 335

His Pro Gly Ile Pro Cys Ile Phe Tyr Asp His Phe Phe Asn Trp Gly
            340                 345                 350

Phe Lys Asp Gln Ile Ala Ala Leu Val Ala Ile Arg Lys Arg Asn Gly
            355                 360                 365

Ile Thr Ala Thr Ser Ala Leu Lys Ile Leu Met His Glu Gly Asp Ala
            370                 375                 380

Tyr Val Ala Glu Ile Asp Gly Lys Val Val Lys Ile Gly Ser Arg Tyr
385                 390                 395                 400

Tyr Asp Val Gly Ala Val Ile Pro Ala Gly Phe Val Thr Ser Ala His
            405                 410                 415

Gly Asn Asp Tyr Ala Val Trp Glu Lys Asn Gly Ala Ala Ala Thr Leu
            420                 425                 430

Gln Arg Ser Ser Glu Lys Asp Glu Leu
            435                 440

<210> SEQ ID NO 13
<211> LENGTH: 6
<212> TYPE: PRT
<213> ORGANISM: Artificial Sequence
<220> FEATURE:
<223> OTHER INFORMATION: Endoplasmic reticulum retention sequence

<400> SEQUENCE: 13

Ser Glu Lys Asp Glu Leu
 1               5
```